(12) United States Patent
Abbas et al.

(10) Patent No.: US 12,390,374 B2
(45) Date of Patent: Aug. 19, 2025

(54) WEARABLE ABSORBENT ARTICLE WITH A CONDUCTOR ARRANGEMENT

(71) Applicant: Essity Hygiene and Health Aktiebolag, Gothenburg (SE)

(72) Inventors: Shabira Abbas, Gothenburg (SE); Tilak Lakshmana, Gothenburg (SE); Karishma Jain, Luleå (SE); Lars-Erik Rudolf Wågberg, Stockholm (SE); Per Anders Larsson, Danderyd (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 18/866,151

(22) PCT Filed: Jun. 3, 2022

(86) PCT No.: PCT/EP2022/065191
§ 371 (c)(1),
(2) Date: Nov. 15, 2024

(87) PCT Pub. No.: WO2023/232263
PCT Pub. Date: Dec. 7, 2023

(65) Prior Publication Data
US 2025/0169997 A1     May 29, 2025

(51) Int. Cl.
*A61F 13/42* (2006.01)
*A61F 13/15* (2006.01)

(52) U.S. Cl.
CPC ........ *A61F 13/42* (2013.01); *A61F 13/15642* (2013.01); *A61F 2013/424* (2013.01)

(58) Field of Classification Search
CPC ................ A61F 13/42; A61F 13/15642; A61F 2013/424; A61F 2013/425; A61F 2013/428
USPC .................................................. 604/358–392
See application file for complete search history.

(56) References Cited

U.S. PATENT DOCUMENTS

2024/0090814 A1*  3/2024  Vitale, III ............. A61B 5/268

FOREIGN PATENT DOCUMENTS

| EP | 3415130 A1 | 12/2018 |
| EP | 3888608 A1 | 10/2021 |
| WO | 2012084987 A2 | 6/2012 |

OTHER PUBLICATIONS

Tekcin et al., Wearable and Flexible Humidity Sensor Integrated to Disposable Diapers for Wetness Monitoring and Urinary Incontinence, Electronics 2022, 11, 1025 (Year: 2022).*
Jain et al., 3D printable composites of modified cellulose fibers and conductive polymers and their use in wearable electronics, Applied Materials Today 30 (2023) 101703 (Year: 2023).*

(Continued)

*Primary Examiner* — Susan S Su
(74) *Attorney, Agent, or Firm* — CANTOR COLBURN LLP

(57) ABSTRACT

This disclosure relates to a wearable absorbent article comprising at least one material layer and a conductor arrangement that is at least partially deposited on, optionally printed onto, the material layer. The conductor arrangement is formed from a composition comprising a dialcohol cellulose and an electrically conductive material.

22 Claims, 27 Drawing Sheets

(56) References Cited

OTHER PUBLICATIONS

International Search Report & Written Opinion for International Application No. PCT/EP2022/065191; International Filing Date: Jun. 3, 2022; Date of Mailing: Feb. 3, 2023; 12 pages.
P.A. Larsson et al: "Towards natural-fibre-based thermoplastic films produced by conventional papermaking"; Green Chemistry, vol. 18, No. 11; Date: Jan. 1, 2016; pp. 3324-3333; XP055421728; ISSN: 1463-9262, DOI: 10.1039/C5GC03068D.
Wakako Kasai et al: Mechanical properties of films made from dialcohol cellulose prepared by homogeneous periodate oxidation:; CELLULOSE, vol. 21, No. 1; Date: Dec. 31, 2013; pp. 769-776; XP055301826; ISSN: 0969-0239, DOI: 10.1007/s10570-013-0153-7.
P.A. Larsson et al: "Towards natural-fibre-based thermoplastic films produced by conventional papermaking"; Green Chemistry, vol. 18, No. 11; Date: Jan. 1, 2016; pp. 3324-3333; XP055421728; XP055630699; ISSN: 1463-9262, DOI: 10.1039/C5GC03068D.
KR OA with English Translation; KR Application No. 10-2024-7042241; Date Mailed: Feb. 12, 2025; pp. 1-6.

* cited by examiner

A

B

A

B

A

B

WEARABLE ABSORBENT ARTICLE WITH A CONDUCTOR ARRANGEMENT

CROSS REFERENCE TO RELATED APPLICATIONS

This application is a National Stage Application of PCT/EP2022/065191, filed Jun. 3, 2022, the contents of which are incorporated by reference in their entirety herein.

TECHNICAL FIELD

The present disclosure relates to a wearable absorbent article, such as a diaper, a sanitary towel, an incontinence garment or a medical dressing, such as a wound dressing, including a conductor arrangement.

The disclosure also relates to a method of manufacturing a wearable absorbent article with a conductor arrangement.

TECHNICAL BACKGROUND

Wearable absorbent articles, such as diapers, sanitary towels, incontinence garments, medical dressings and the like, have wide-spread utility in both domestic and institutional settings for such purposes as the care of infants, the management of menstrual discharge, the management of bodily efflux or exudate and the management of incontinence. However, a known problem associated with the use of absorbent articles is that the articles have a finite capacity for absorption which, if exceeded, will cause the absorbent article to become ineffective, e.g., to leak, or at least to fail to absorb further.

Therefore, users of such articles, or their carers, predict when an absorbent article is nearing its absorbent capacity and then take steps to replace the article before capacity is reached. In situations where there are many users of such absorbent articles with relatively fewer carers, such as in institutional settings, the management of the capacity of the various absorbent articles in use becomes a significant administrative burden.

It can be very difficult for a user or carer to accurately predict or determine the state of an absorbent article, in terms both of utilised absorbent capacity and the need for the article to be replaced. Even where the absorbent demands on the article are reasonably predictable, a period of record-keeping and experimentation is required before a pattern may be established and appropriate absorbent articles may be provided.

Systems which are able to alert the user or carer to saturation or impending saturation of the absorbent article are therefore of benefit. Such systems may take the form of wetness sensors for detecting wetness within the absorbent article. The wetness sensors may use a conductor arrangement provided in the wearable absorbent article for detecting wetness by measuring the resistance between different conductors of the conductor arrangement. In this way, wetness sensors can be capable of determining both the amount of wetness and the location where the wetness event has occurred in the absorbent article.

One approach to an absorbent article containing a wetness sensor is described in WO 2012/084987. It can also be contemplated to include other sensors in wearable absorbent articles, such as infection sensors, hydration level sensors, etc.

The application of a wetness sensor does increase the costs of the absorbent articles, and also the manufacturing process is thereby rendered more complicated than for absorbent articles without a wetness sensor.

There is, hence, a need for improved wearable absorbent articles that address at least one of the above-mentioned shortcomings.

SUMMARY

Aspects of the above-mentioned object are achieved by a wearable absorbent article in accordance with the present disclosure.

One aspect of the present disclosure relates to a wearable absorbent article including at least one material layer; and a conductor arrangement that is at least partially deposited on the material layer. The conductor arrangement is formed from a composition including a dialcohol cellulose and an electrically conductive material.

According to some embodiments, the conductor arrangement is at least partially printed onto material layer.

According to some embodiments, the conductor arrangement is fully deposited on a plurality of material layers including the at least one material layer. The conductor arrangement may be fully deposited on the at least one material layer.

According to some embodiments, the conductor arrangement is fully printed on a plurality of material layers including the at least one material layer. The conductor arrangement may be fully printed on the at least one material layer.

The composition deposited on (e.g. printed onto) the at least one material layer or the plurality of material layers may an electrically conducting bio-ink that includes modified cellulose fibers, wherein the cellulose has been partly converted to dialcohol cellulose, hereafter referred to as dialcohol-modified cellulose (DALC) fibers. DALC fibers are highly flexible, ductile and can be melt-processed. Manufacturing the conductive arrangement of the absorbent article may allow the energy intensive step of nanocellulose preparation to be omitted. Furthermore, the content of the conductive material required may be reduced without compromising the conductivity.

The absorbent article may be manufactured cost-efficiently and in an environment-friendly manner, as less energy may be consumed during the manufacturing process than compared to when manufacturing other absorbent articles including a conductive arrangement.

According to some embodiments, the conductor arrangement includes a sensing device or a part of a sensing device. The sensing device may include two elements and may be configured to measure the resistance between two elements. According to some embodiments, the sensing device may be an impedance-based sensor.

The sensing device may, for some embodiments, be configured to detect one or several of: infections, microbial growth, temperature, hydration level, etc. The sensing device may be a wetness sensor or another type of sensor.

According to some embodiments, the wearable absorbent articles includes a sensing device or a part of a sensing device that is in electrical contact with the conductor arrangement. The sensing device may include two elements and may be configured to measure the resistance between two elements. According to some embodiments, the sensing device may be an impedance-based sensor.

A value of impedance measured by the sensing device may vary (e.g., decrease) in response to the introduction of liquid, such as urine, into the wearable absorbent article (e.g., a diaper or a female hygiene article). The sensing device may, hence, be used for detecting the presence of a liquid, such as urine, in (a portion of) the wearable absorbent article. When the sensing device is configured to measure impedance, it may be deposited (printed) on the at least one or several material layer such that no galvanic contact between the sensing device and the liquid is needed for detecting the presence of liquid. In other words, a liquid absorbed by an absorbent layer of the wearable absorbent article may be detected remotely.

When using an additional sensing device that is positioned on the wearable absorbent article to be in electrical contact with the conductive arrangement provided thereon, the concept of detecting a liquid by virtue of a sensing element for measuring an impedance allows obtaining a configuration in which the sensing device is positioned on a garment facing surface of the wearable absorbent article. The latter location may, in turn, be associated with reduced effort as regards an application and/or removal of the sensing device. Moreover, the attaching and/or detaching may take place even while a person such as an infant or a patient wears the wearable absorbent article.

According to some embodiments, the conductor arrangement includes an additional sensing device or a part of an additional sensing device. The additional sensing device may include two elements and may be configured to measure the resistance between two elements. According to some embodiments, the additional sensing device may be an impedance-based sensor.

According to some embodiments, the wearable absorbent articles includes an additional sensing device or a part of an additional sensing device that is in electrical contact with the conductor arrangement. The additional sensing device may include two elements and may be configured to measure the resistance between two elements. According to some embodiments, the additional sensing device may be an impedance-based sensor.

The presence of an additional sensing device may promote an increased measurement accuracy. That is, if an additional second sensing device is provided in addition to the sensing device, a measurement of, e.g., an impedance may be enabled at at least two portions of the wearable absorbent article. It may, hence, be possible to determine the presence of a liquid in the wearable absorbent article even if the liquid has not been introduced into a portion associated with a location of one of the sensing devices. Therefore, it may be less likely to receive a "false negative" measurement result.

Moreover, the presence of more than one sensing device may allow drawing conclusions as regards a saturation of the wearable absorbent article.

According to some embodiments, the conductive arrangement is provided on the body-facing side of the wearable absorbent article. This may allow detecting the presence of a fluid by direct (galvanic) contact with the fluid.

According to some embodiments, the conductive arrangement is provided on the garment-facing side of the wearable absorbent article. This may allow detecting the presence of a fluid indirectly, i.e., without (galvanic) contact with the fluid.

The wearable absorbent article may include one or several fluid absorption regions for absorbing a fluid, and an electronic device or a mounting position for mounting an electronic device, wherein the conductor arrangement electrically connects the electronic device or the mounting position for mounting an electronic device to at least one sensing location for detecting wetness of the at least one or of a two or more of the fluid absorption regions.

The electronic device may be the above-mentioned sensing device. The electronic device may be a device for transmitting a signal to an external device.

The conductor arrangement may include a plurality of elongate conductor lines extending along an extension direction. Each of the conductor lines may be electrically connected to a respective electrode, and the electrodes may be arranged in contact with the fluid absorption region of the wearable absorbent article The electronic device may be configured to detect a wetness at one or more locations within the fluid adsorption region by measuring an electrical resistance between two of the electrodes through the conductor lines.

At least some of the conductor lines may differ in terms of cross-section, thus having different electrical resistances.

The conductor lines may have lengths in the respective extension directions in the range of 1 cm to 60 cm and/or cross-sectional areas perpendicular to the respective extension directions in the range of 0.01 mm$^2$ to 1.00 mm$^2$.

The fluid absorption region may include an absorbent core, and at least a part of the conductor arrangement may be arranged so as to be electrically insulated from the absorbent core.

The electronic device may include a wetness detection unit that is removably attached to the remainder of the wearable absorbent article or is embedded within the remainder of the wearable absorbent article.

The wearable absorbent article may be a diaper, a sanitary towel, or an incontinence garment.

The wearable absorbent article may be a medical dressing, such as a wound dressing. The medical dressing may include a wound contacting layer, an absorbent core, and a backing layer.

According to some embodiments, the conductor arrangement includes a ground electrode and a capacitor electrode, and the ground electrode may form a closed loop around the capacitor electrode.

The material layer may include at least one item selected from the group consisting of flexible materials, such as non-wovens, films, tissue paper and fabrics.

The conductor arrangement may include between 5 wt % and 70 wt % of the electrically active material. The conductor arrangement may include between 30 wt % and 95 wt % of the dialcohol cellulose. The conductor arrangement may include between 10 wt % and 80 wt % of a plasticizer.

As used herein, the term "plasticizer" commonly refers to a substance or material incorporated in the matrix forming material to increase its flexibility or workability. Many plasticizers tend to decrease the intermolecular forces between polymer chains, resulting in the increased flexibility and compressibility, or they may exert a plasticizing effect since they cause discontinuities in a polymer matrix. Examples of classes of plasticizers are saccharides (mono-, di- or oligosaccharides), alcohols, polyols, acid, salts, lipids and derivatives (such as fatty acids, monoglycerides, esters, phospholipids) and surfactants. Specific examples of suitable plasticizers include but are not limited to: glucose, fructose, sorbitol, polyethylene glycol, glycerol, propylene glycol, lactitol, sodium lactate, hydrated hydrolyzed starches, trehalose, or combinations thereof such as honey. Other suitable plasticizers for use in the present disclosure include DMSO and ionic liquids.

The electrically conductive material may include a conductive polymer. The conductive polymer may be PEDOT: PSS. "PEDOT:PSS" is a polymeric compound, also called a polymer complex, including poly-3,4-ethylenedioxythiophene (PEDOT) and polystyrene sulfonate (PSS) in any ratio. PEDOT:PSS is available from multiple suppliers and is commonly used in conductive bio ink as it is easy to use. A PEDOT:PSS ratio of 1:2.5 may be used to form the electrically conductive material, however, it is generally understood that changing the ratio is also possible.

Conductive polymers such as PEDOT:PSS as a component used for the conductive arrangement may offer advantages, as they are electroactive components that offer benefits in terms of their processability, electrochemical properties, and charge transfer abilities. Such polymers may have required doping with solvents such as ionic liquids, concentrated sulfuric acid, or dimethyl sulfoxide (DMSO), to increase their electronic conductivity for application in electronic devices. However, in the composition used for the conductive arrangement in accordance with the present disclosure, addition of an organic solvent may not be required. This may offer benefits in terms of manufacturability, cost-efficiency, and environment-friendliness.

According to some embodiments, the conductor arrangement has an electric conductivity of at least 0.05 S/cm. It may have an electric conductivity of at least 0.1 S/cm. It may have an electric conductivity of at least 0.5 S/cm. It may have an electric conductivity or at least 1 S/cm.

The dialcohol cellulose may include fibers having a diameter of at least 1 µm (and, according to some embodiments, no fibers with smaller diameters). According to some embodiments, the dialcohol cellulose includes fibers having a diameter of at least 5 µm (and, according to some embodiments, no fibers with smaller diameters). The dialcohol cellulose may include fibers having a diameter of at least such as at least 8 µm (and, according to some embodiments, no fibers with smaller diameters). The dialcohol cellulose may includes fibers having a diameter of at least 12 µm (and, according to some embodiments, no fibers with smaller diameters).

The dialcohol cellulose may includes nanofibrils having a diameter of less than 1000 nm, optionally less than 500 nm, or less than 200 nm, or less than 100 nm, or 50 nm.

The plasticizer may include a polyol.

The polyol may be selected from the group consisting of a glycerol, a sorbitol and an erythritol.

The polyol may include glycerol.

The plasticizer may include DMSO.

The plasticizer may include ionic liquids.

When the conductive arrangement includes an electrically conducting polymer, the electrically conducting polymer may include one or more polymers selected from the group consisting of polyphenylenes, polypyrenes, polyazulenes, polynaphthalenes, polyacetylenes (PAC), poly-p-phenylene vinylene (PPV), polypyrroles (PPY), polyazepines, polyanilines (PANI), polythiophenes (PT), poly-3,4-ethylenedioxythiophene (PEDOT), toluenesulfonyl (Tos) and a polystyrene sulfonates (PSS).

The conductive arrangement may include between 10 wt % and 50 wt % of the electrically conductive polymer.

The conductive arrangement may include at least 40 wt % of the electrically conducting polymer.

The conductive arrangement may include an electrically conducting carbon.

The electrically conducting carbon may be selected from the group consisting of 1D carbons, 2D carbons, and 3D carbons. The 3D carbon may be a graphite. The 2D carbon may be a graphene. The 1D carbon may be a carbon nanotube.

The conductive arrangement may include an electrically conducting 2D material. The electrically conducting 2D material may be selected from the group consisting of a graphene, a MXenes and a Molybdenum disulfide (MoS2).

Another aspect of the present disclosure relates to a method of manufacturing a wearable absorbent article. The method includes the steps of providing an absorbent article including at least one material layer, and of depositing a composition, including a dialcohol cellulose and an electrically conductive material, on the at least one material layer, to form a conductor arrangement on the at least one material layer.

According to some embodiments, the composition is deposited on the at least one material layer by any one or several of the following techniques: 3D-printing, 2D-printing, screen printing, stencil printing, blade-coating, melt-processing molding, slot die coating, inkjet printing, laser printing, solution processing, vacuum filtration, solvent casting and paper making techniques.

The composition may be at least partly dried before, during and/or after applying the composition.

The composition may be at least partly cured before, during and/or after applying the composition.

The method may further include (an) additional step(s) of adding a cross-linking agent before, during and/or after applying the composition.

As used herein, the terms "cross-linking agent" or "cross-linker" refers to chemical entities capable of forming cross-linking chains between polymers; as well as agents capable of providing cross-linking of polymer chains in the presence of the appropriate reagents, such as gamma-irradiation, or other types of electromagnetic radiation, or electron bombardment.

The cross-linking agent may be added before, during and/or after applying the composition.

Another aspect of the present disclosure relates to an absorbent article manufactured according to any of the aspects of the method in accordance with the present disclosure.

Additional advantages and features of the present disclosure, that can be realized on their own or in combination with one or several features discussed above, insofar as the features do not contradict each other, will become apparent from the following description of particular embodiments.

BRIEF DESCRIPTION OF THE DRAWINGS

For a better understanding of the present disclosure and to show how the same may be carried into effect, reference will now be made, by way of example only, to the accompanying drawings, in which:

The description is given with reference to the accompanying drawings, in which:

FIG. 2a depicts a conductive arrangement printed onto a material layer of an embodiment of a wearable absorbent article in accordance with the present disclosure;

FIG. 2b is an enlarged view of a part A of FIG. 1a;

FIG. 13a shows relative resistance as a function of stretching a 3D serpentine pattern printed using a composition for use in a conductive arrangement deposited on a wearable absorbent article;

FIG. 13b shows a simple conductive function of the serpentine pattern of FIG. 13a;

FIG. 1a depicts a top view of a wearable absorbent article in accordance with the present disclosure. This embodiment is a diaper 1.

Figure 1A:
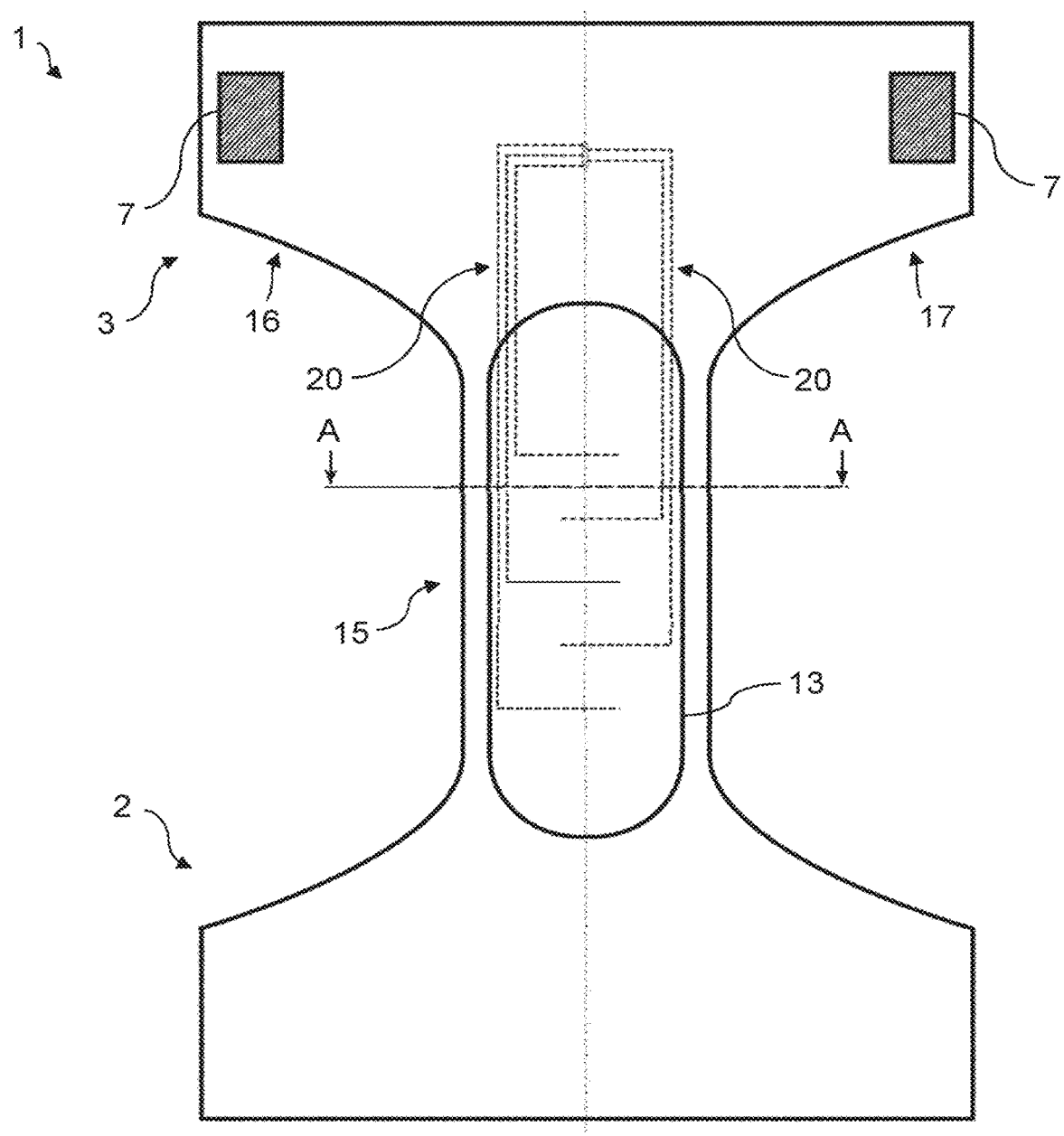
FIG. 1a depicts a top view of a wearable absorbent article in accordance with an embodiment in accordance with the present disclosure.

The diaper 1 includes a main portion 15, a first side portion 16, a second side portion 17, and attachment members 7. The main portion 15 is elongate in a first direction. The first direction is parallel to a longitudinal center line of the wearable absorbent article. The longitudinal center line extends from a front side 2 of the absorbent article, facing a front side of the wearer in use thereof, to a back side 3 of the absorbent article, facing a back side of the wearer in use thereof.

The first side portion 16 and the second side portion 17 extend away from the main portion 15 along a second direction perpendicular to the first direction. The first side portion 16 and the second side portion 17 extend away from the main portion 15 on opposite sides of the main portion 15. An attachment member 7 is disposed on both side portions 16, 17.

Figure 1B:
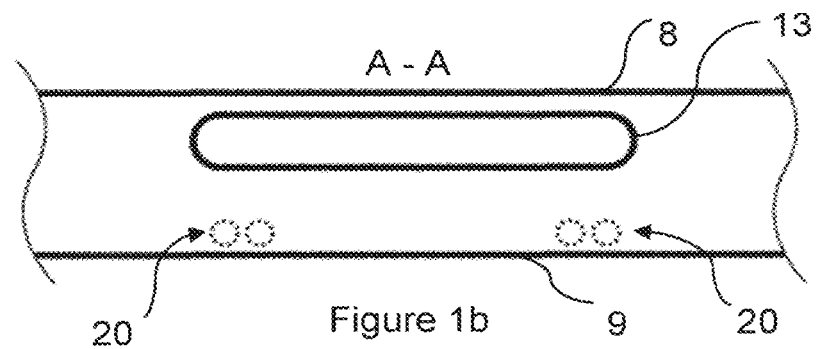
FIG. 1b depicts a sectional view along the line A-A in FIG. 1.

FIG. 1b depicts a sectional view along line A-A of FIG. 1a.

The diaper 1 has a liquid permeable top layer 8 adapted to face the wearer during use and to allow a fluid, such as urine or other bodily fluids, to pass through, a liquid impermeable bottom layer 9 opposite to the top layer 8, which is adapted to prevent the fluid from passing through, and an absorbent core 13 located between the bottom layer 9 and the top layer 8 for absorbing the fluid.

The diaper 1 is configured to be worn around the waist of a user by attaching the side portions 16, 17, to the main portion 15 using the attachment members 7.

Moreover, the diaper 1 is provided with a conductive arrangement 20 printed onto the bottom layer 9.

While a diaper has been described in connection with FIGS. 1a and 1b, the present disclosure also encompasses other embodiments of wearable absorbent articles provided with a conductor arrangement in accordance with the present disclosure. In particular, a conductor arrangement similar or identical to the one of FIGS. 1a and 1b may, for example, be printed onto medical dressing, such as a wound dressing, or on a sanitary towel or an incontinence garment.

FIG. 2a depicts a conductive arrangement 20 printed onto a material layer of a first embodiment of a wearable absorbent article in accordance with the present disclosure.

The conductive arrangement may, for example, be printed on a diaper, a sanitary towel, an incontinence garment, or a medical dressing. The example of a diaper will be discussed in further details.

For example, the conductive arrangement 20 may be printed onto one of the layers of the diaper 1 of FIG. 1. A different embodiment is, for example, a wound dressing with the conductive arrangement of FIG. 2a printed on a layer thereof.

The conductor arrangement 20 is formed from a composition including a dialcohol cellulose and an electrically conductive material, and it forms part of a sensing device for detecting wetness in the diaper.

The conductor arrangement 20 includes a plurality of elongate conductor lines and electrode lines, each of the electrode lines being electrically connected to a respective one of the conductor lines. The conductor arrangement 20 has attached thereto a wetness detection unit (not shown), a control unit for controlling the wetness detection unit (not shown), and a power source (not shown) 0 providing power to the control unit and the wetness detection unit.

The conductor arrangement may further have a transmitter for transmitting information relating to the wetness detected by the wetness detection unit or other relevant information. The conductor arrangement may further have a receiver for receiving information, such as instructions.

The conductor arrangement includes between 5 wt % and 70 wt % of the electrically active material, between 30 wt % and 95 wt % of the dialcohol cellulose, and, optionally, between 10 wt % and 80 wt % of a plasticizer. The electrically conductive material includes a conductive polymer. The conductive polymer includes poly-3,4-ethylenedioxythiophene and polystyrene sulfonate.

The conductive arrangement is printed onto a material layer of the diaper 1 in the main portion 15 of the diaper 1. It may, for example, be printed onto a layer facing the absorbent core 13, on a body-facing side, or on a garment-facing side, depending on the type of sensing technology being used.

The power source may hold an energy store in the form of electrical energy and/or a chemical energy. The power source may be any type of power source, such as a cell, a battery and/or a capacitor. For example, the power source may be a flexible paper cell/battery, such as those provided by Blue Spark Technologies (OH, US), Enfucell Oy (FI), GS Nanotech (KR) or Cymbet (MN, US).

The conductor arrangement 20 has an electric conductivity of at least 0.05 S/cm, optionally at least 0.1 S/cm, or at least 0.5 S/cm, or at least 1 S/cm. The dialcohol cellulose includes fibers having a diameter of at least 1 µm, such as at least 5 µm, such as at least 8 µm, such as at least 12 µm.

The conductor arrangement 20 includes a plurality of elongate conductor lines 4, each conductor lines 4 extending along the same extension direction. The extension direction of the conductors 4 is parallel to the longitudinal center line of the wearable absorbent article (see, e.g., the diaper 1 of FIG. 1). Each conductor lines 4 has been printed onto a material layer of the wearable absorbent article.

In the case of the embodiment of FIG. 2a, the conductor lines 4 have different lengths in the extension direction. The conductor lines 4 that are longer in the extension direction may have lower electrical resistances per unit length than those that are shorter in the extension direction.

In particular, as is schematically shown in the enlarged view of FIG. 2b, the longer conductor lines 4 have cross-sectional areas perpendicular to the extension direction that are larger than the cross-sectional areas perpendicular to the extension direction of the shorter conductors 4. In this way, the differences in resistance, i.e., overall or total resistance, of the conductor lines 4 associated with the differences in lengths can be reduced or even eliminated in a particularly simple and efficient manner. However, for other embodiments, conductor lines 4 with different lengths may have identical cross-sections.

Further, those of the conductor lines 4 which have larger lengths in the extension direction may be made of materials, e.g., metals and/or metal alloys, having lower electrical resistivities than the materials, e.g., metals and/or metal alloys, of which those of the conductor lines 4 are made which have smaller lengths in the extension direction.

The cross-sectional areas and/or the materials of the conductors 4 may be chosen such that all of the conductors 4 have substantially the same electrical resistance.

Each of the conductor lines 4 of the conductor arrangement 20 is electrically connected to an electrode line 6, as is shown in FIG. 2a. Specifically, each of the electrode lines 6 is electrically connected to a respective conductor line 4 at the distal end of the conductor line 4 in the extension direction thereof, i.e., the end of the conductor line 4 which is disposed further away from the wetness detection unit (not shown).

All of the electrode lines 6 extend along the same extension direction. The extension direction of the electrode lines 6 is substantially perpendicular to the extension direction of the conductor lines 4. All of the electrode lines 6 have substantially the same length in the extension direction.

The conductor lines 4 and the electrodes 6 are disposed between an insulating substrate 24 and an insulating layer 25 so that the conductor lines 4 are covered by the insulating layer 25 and the electrode lines 6 are exposed through the openings 26. In this way, it can be reliably ensured that the conductor lines 4 are electrically insulated from the absorbent core of the wearable absorbent article, while the electrodes 6 can be arranged in contact with the absorbent core in a simple and efficient manner. In this way, upon the occurrence of a wetness event in the absorbent core, an electrical contact is established between a respective one or respective ones of the electrode lines 6 and the absorbent core.

The wetness detector (not shown) is configured to detect the wetness at the one or more locations within the absorbent core by measuring the electrical resistance between adjacent ones of the electrode lines 6, i.e., electrode lines 6 which are adjacent to each other, through the conductor lines 4. In particular, this electrical resistance is measured at electrical contacts 27, each of which is electrically connected to a respective conductor line 4 at a proximal end of the conductor line 4 in the extension direction thereof, i.e., at the end of the conductor line 4 which is disposed closer to the wetness detection unit (see FIGS. 2a and 2b). These electrical contacts 27 are arranged adjacent to each other along the extension direction of the conductor lines 4, i.e., along the longitudinal center line of the wearable absorbent article.

Figure 2:
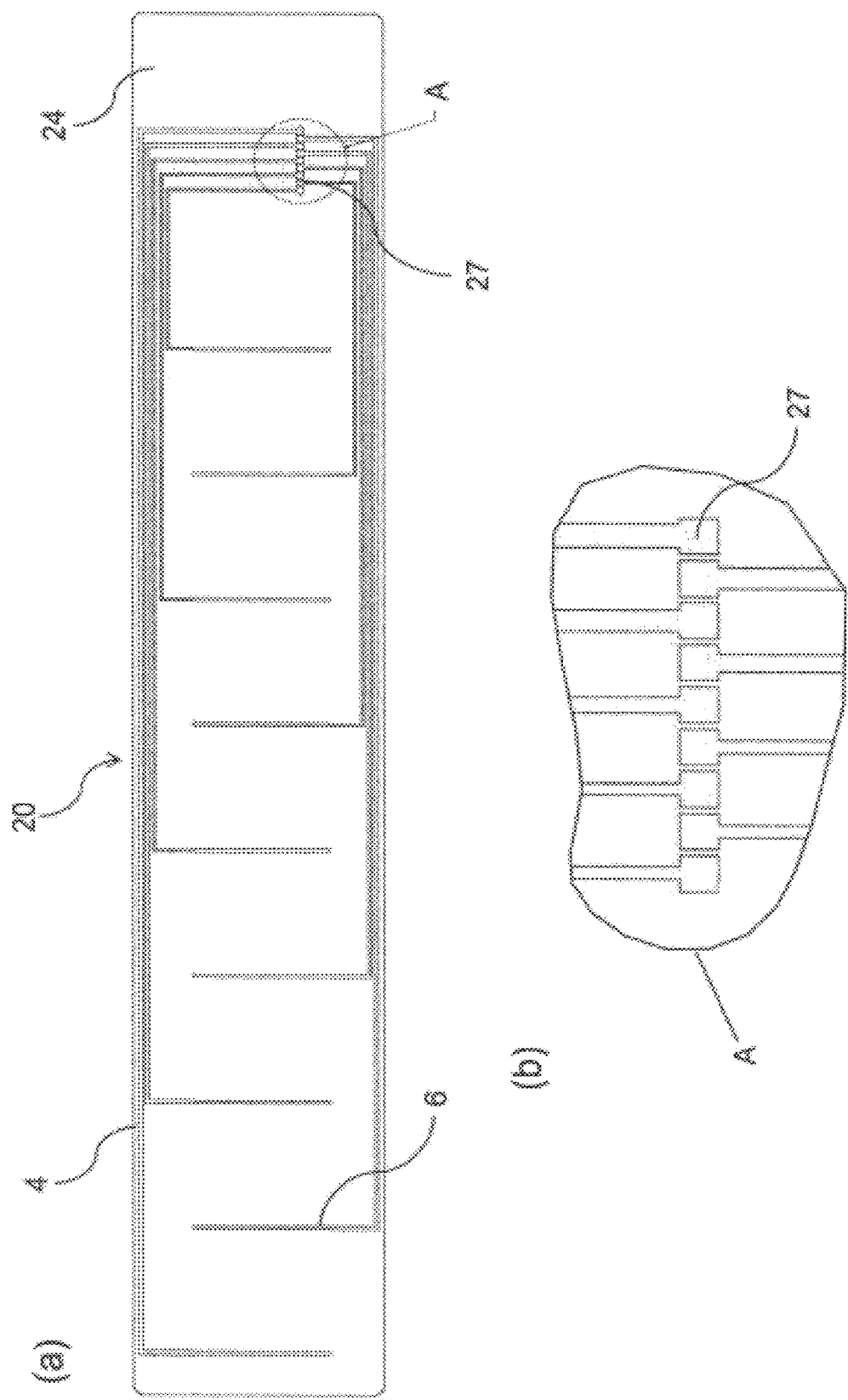

For the embodiment of FIG. 2, the conductive arrangement 20 may be printed onto a material layer of a diaper in a position such that the electrode lines 6 are in contact with the absorbent core of the diaper, while the conductor lines 4 are electrically insulated from the absorbent core by an insulating layer 25. Upon the occurrence of a wetness event in the absorbent core, an electrical contact is established between respective ones of the electrode lines 6 and the absorbent core. In this way, an electrical contact is established between at least two of the electrode lines 6 through the absorbent core.

The wetness detection unit (not shown) is configured to detect the wetness at the one or more locations within the absorbent core by measuring the electrical resistance between at least two, e.g., adjacent ones, of the electrode lines 6 through the conductor lines 4. The electrical resistance is measured at the electrical contacts 27 (see FIGS. 2a and 2b), as has been detailed above.

Figure 3A:
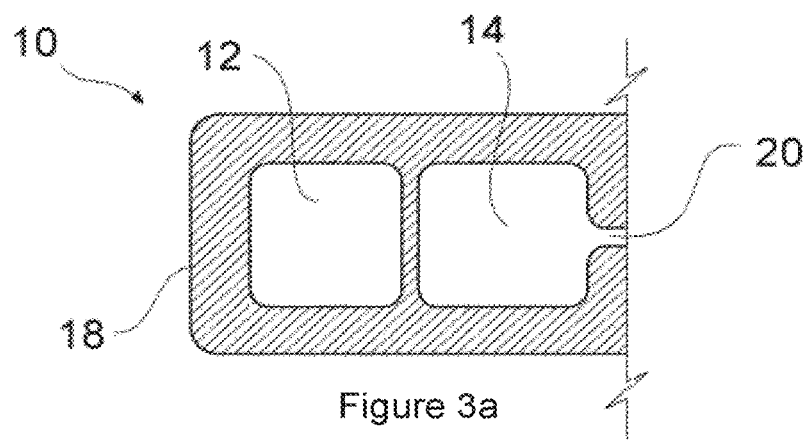
FIG. 3a depicts a conductive arrangement printed onto a material layer of an embodiment of a wearable absorbent article in accordance with the present disclosure.

FIG. 3a depicts a conductive arrangement printed onto a material layer of an embodiment of a wearable absorbent article in accordance with the present disclosure. The conductive arrangement may, for example, be printed on a diaper, a sanitary towel, an incontinence garment, or a medical dressing.

Figure 3B:
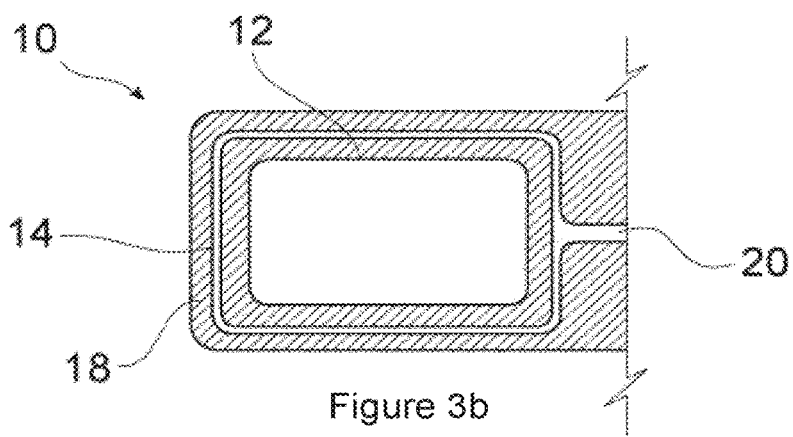
FIG. 3b depicts a conductive arrangement printed onto a material layer of an embodiment of a wearable absorbent article in accordance with the present disclosure.

FIG. 3b depicts a conductive arrangement printed onto a material layer of an embodiment of a wearable absorbent article in accordance with the present disclosure. The conductive arrangement may, for example, be printed on a diaper, a sanitary towel, an incontinence garment, or a medical dressing.

The conductive arrangements depicted in FIGS. 3a and 3b are configured to include sensing elements 10, and respective shielding components 18 are continuously provided between the respective ground elements (including the respective ground electrode lines 12 and the respective ground lines 20), and the respective signal lines 14, such that there is no portion of the sensing elements 10 in which the respective shielding component 18 is not provided between the ground element and the signal line 14.

As explained above, the conductive arrangements deposited at least partially onto one or several material layers of a wearable absorbent article in accordance with the present disclosure are formed from a composition including dialcohol cellulose and an electrically conductive material.

Figure 4A:
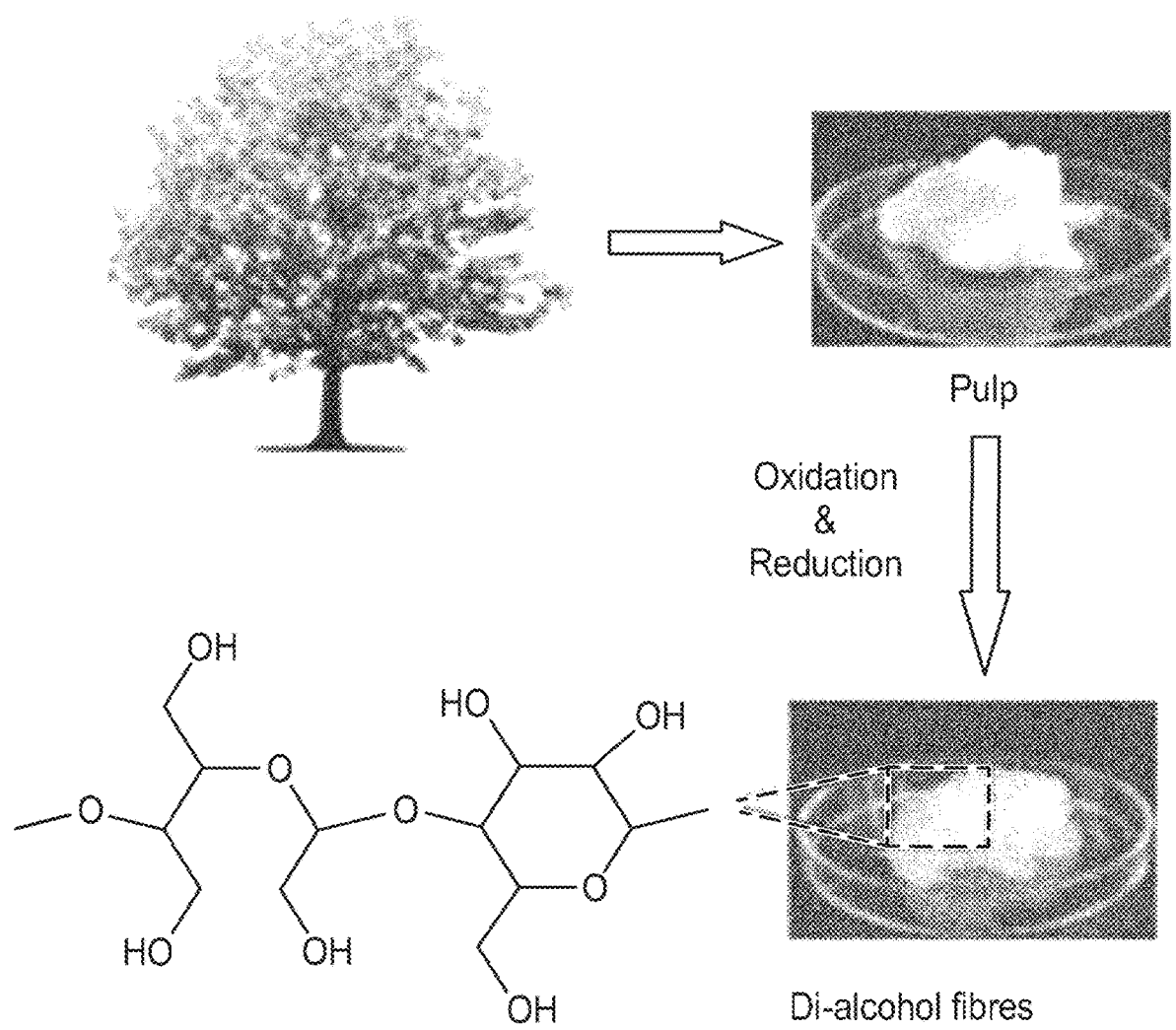
FIG. 4a shows part of a schematic process for preparing dialcohol-modified cellulose fibers for use in a conductive arrangement on a wearable absorbent article.
Figure 5A:
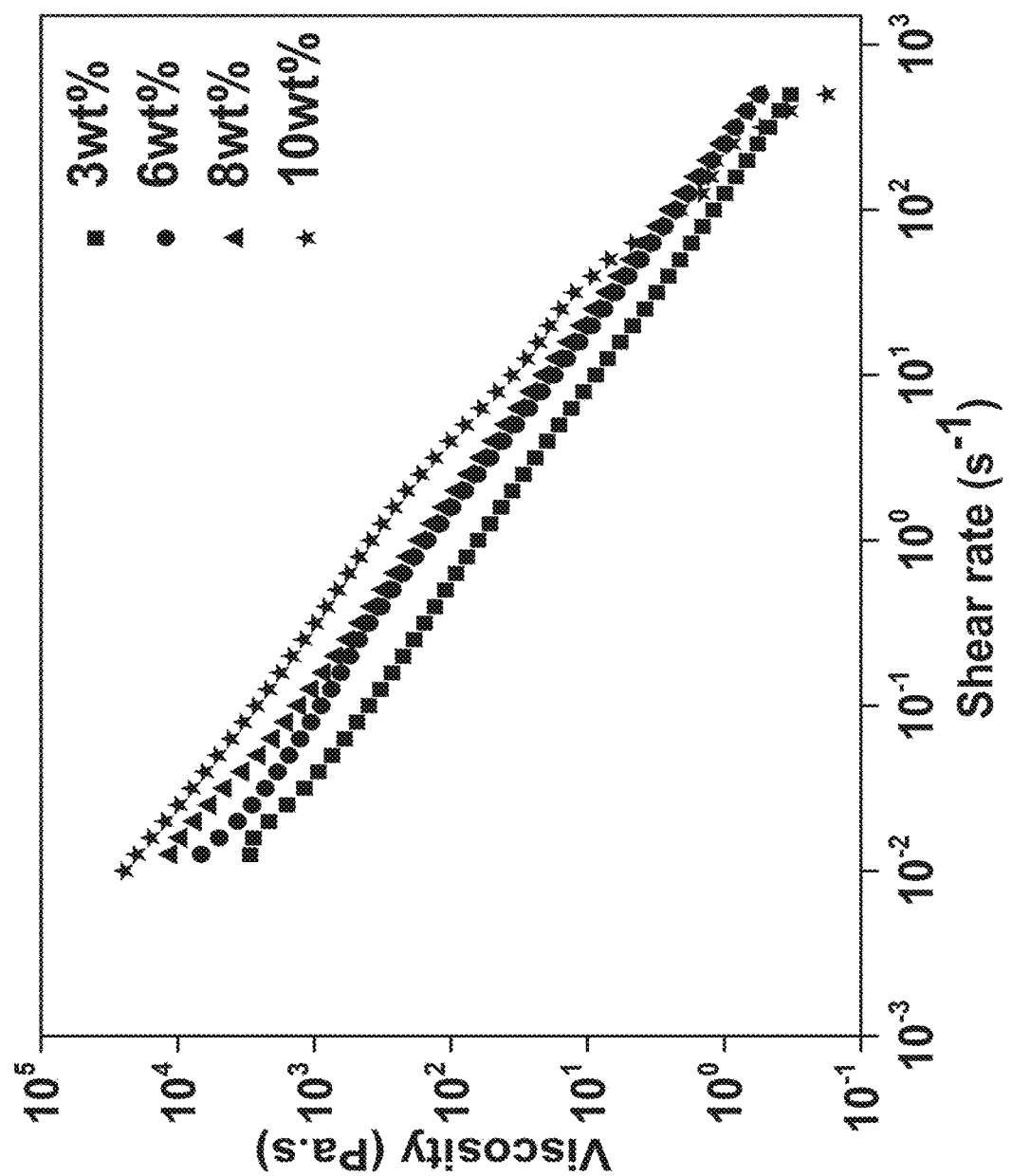
FIG. 5 shows results of a rheology analysis of a 3D conducting ink at different solids content obtained from a composition used in a conductive arrangement deposited on a wearable absorbent article.
Figure 5B:
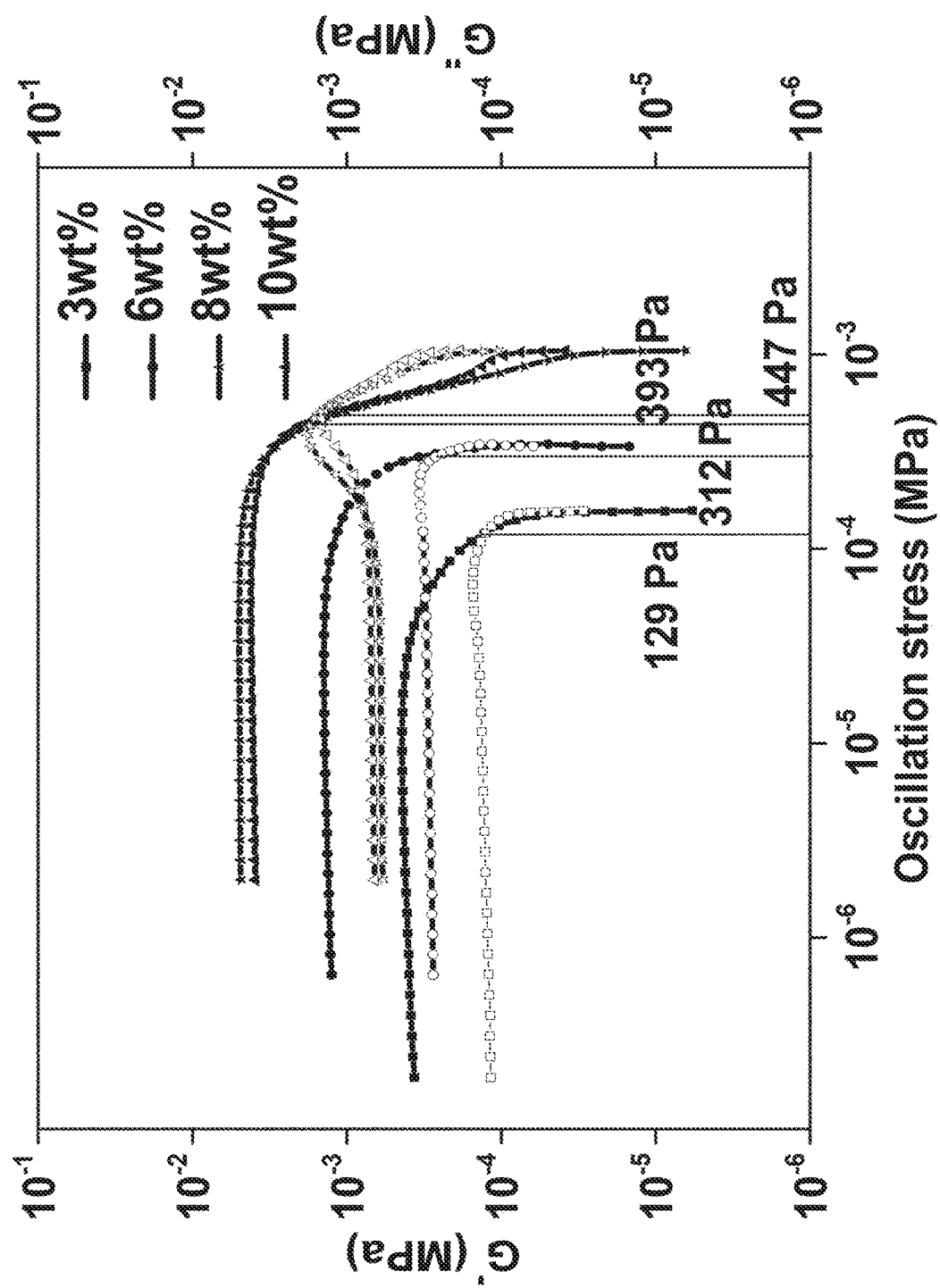
Figure 5C:
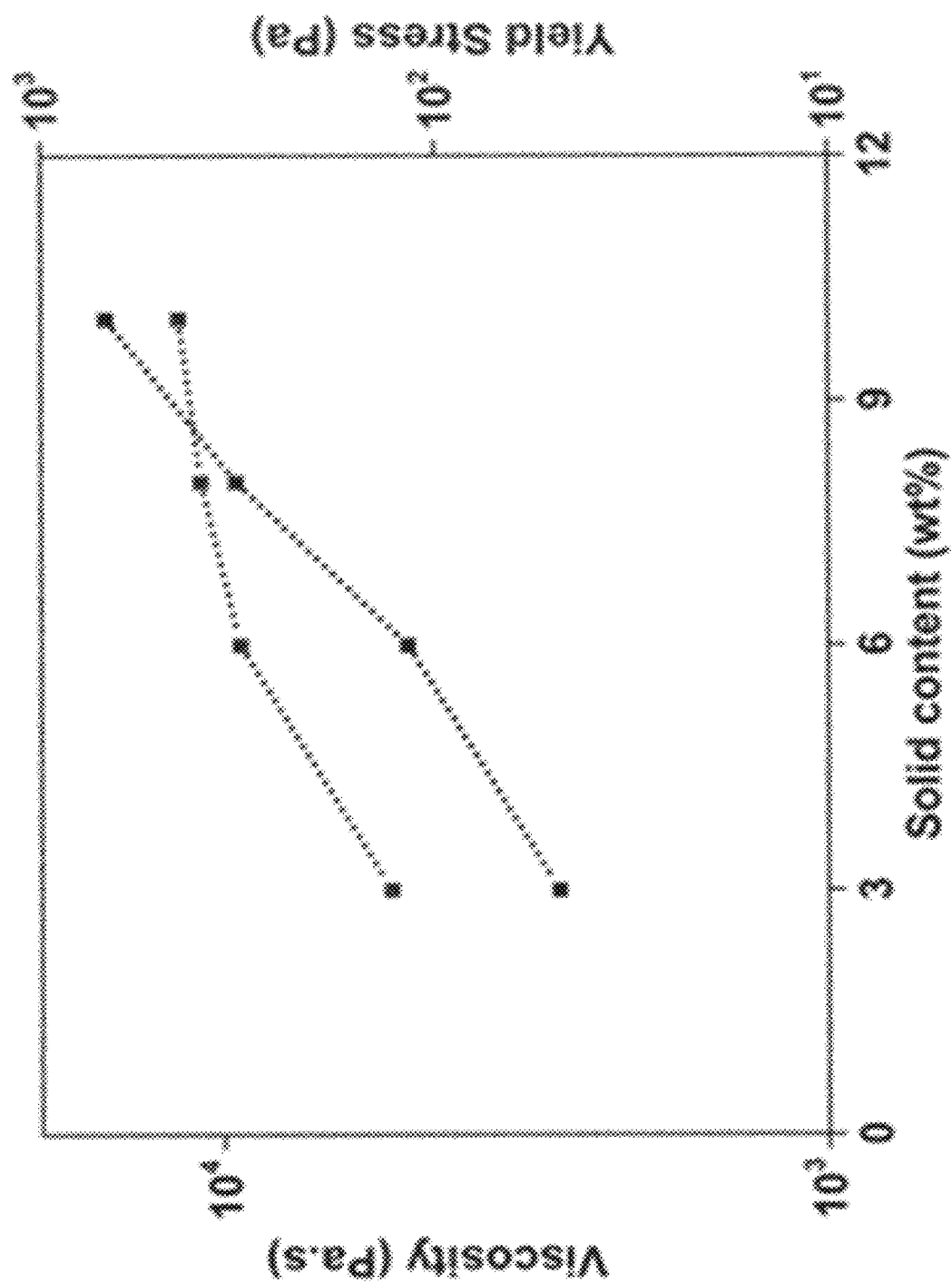
Figure 5D:
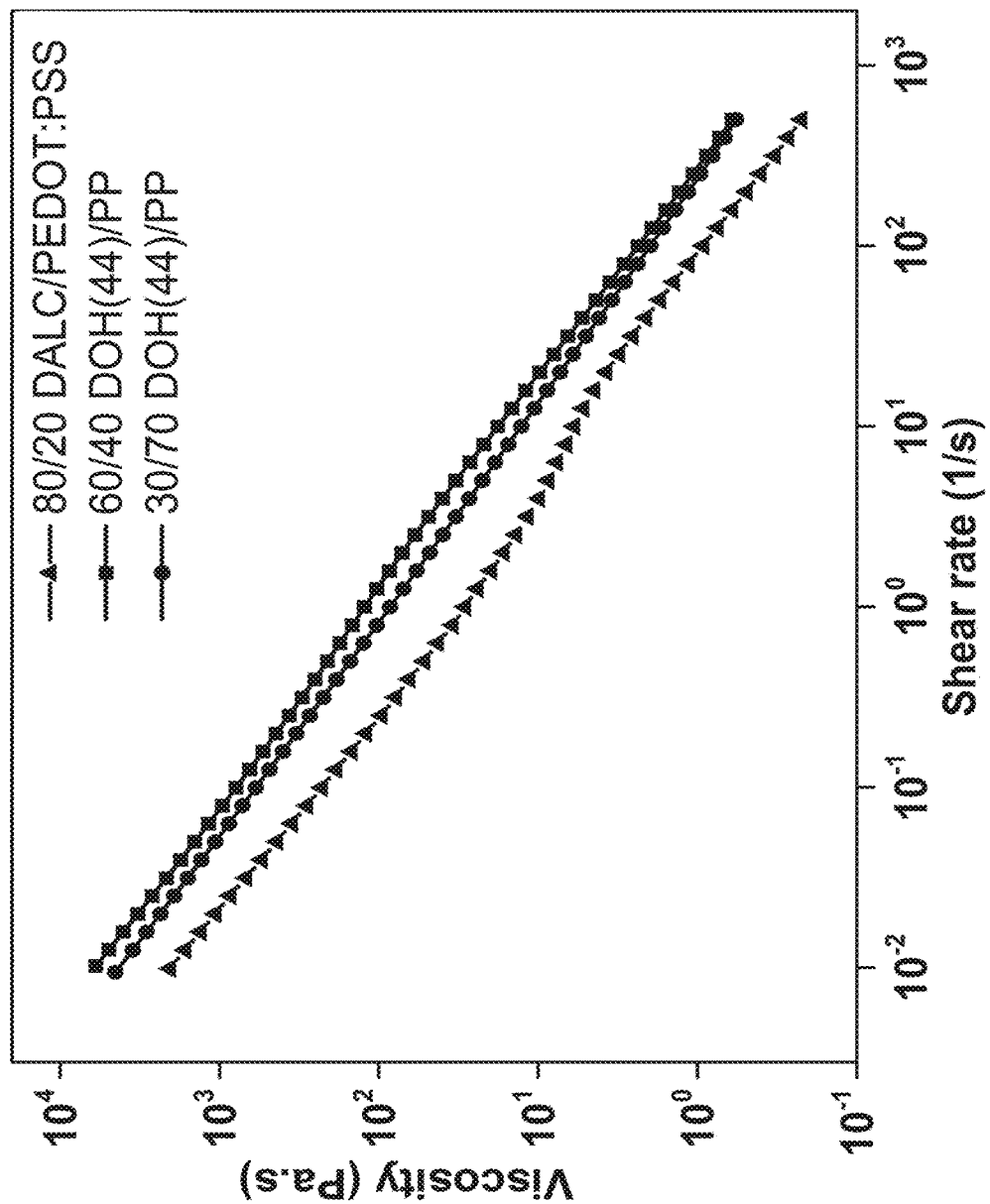
Figure 6:
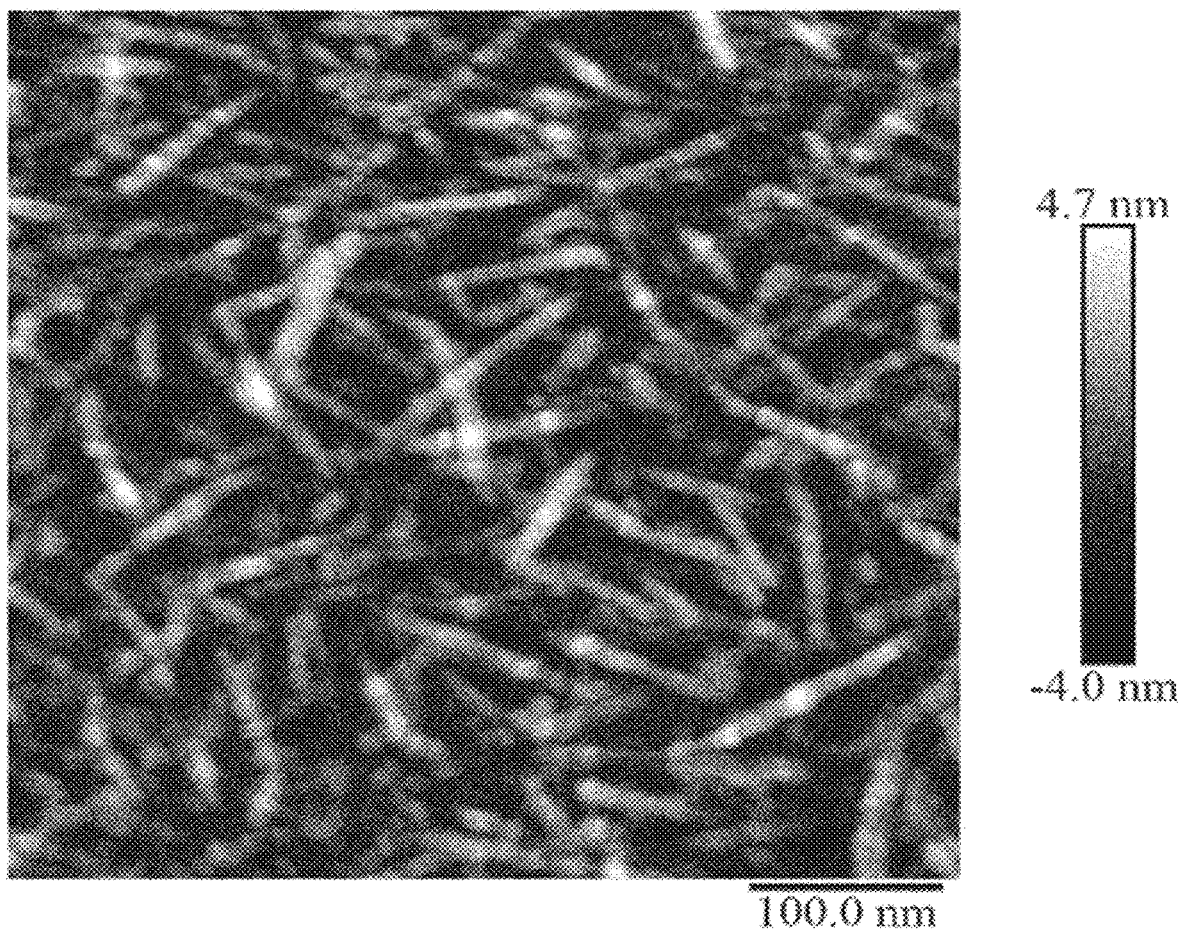
FIG. 6 shows an AFM image of PEDOT:PSS particles decorated on dialcohol cellulose nanofibrils in the fibers.

"Dialcohol cellulose" or "DALC" or "dialcohol modified cellulose fibers" refers to modified cellulose that may be obtainable, for example, by a method, as illustrated in FIGS. 4a and 5b. This method includes oxidizing cellulose in a fiber suspension to dialdehyde cellulose followed by reduction of dialdehyde cellulose to obtain the dialcohol cellulose. Some of the methods to obtain DALC are further discussed in patent application WO2018/135994. The terms also incorporate DALC nanofibrils, cellulose-based nanofibrils obtainable by microfluidization or mechanical processing of DALC fibers. It is to be understood that while both cellulose nanofibrils and fibers that have been dialcohol modified can be referred to as dialcohol cellulose, nanofibrils have a diameter of a few nanometers, such as less than 1000 nm, preferably less than 500 nm, or less than 200 nm, or less than 100 nm, or 50 nm, while fibers are in the micrometer range, may have but not limited to a diameter of at least 1 μm, such as at least 5 μm, such as at least 8 μm, such as at least 12 μm. The length of the fibers and nanofibrils may be in a micrometer or a millimeter range.

In general when referring to DALC cellulose it is understood that a certain amount of the cellulose has been modified. Typically the modification desired depends on the application. However, generally for the applications disclosed herein a degree of modification or degree of substitution 10%-50% is sufficient. However, lower or even higher degrees of substitution or modification may also be used.

"PEDOT:PSS" is a polymeric compound, also called a polymer complex, including poly-3,4-ethylenedioxythiophene (PEDOT) and polystyrene sulfonate (PSS) in any ratio. PEDOT:PSS is available from multiple suppliers and may be used in conductive bio ink as it is easy to use. If nothing else is mentioned, a PEDOT:PSS ratio of 1:2.5 is used, however, it is generally understood that changing the ratio is possible and considered within the scope of the present disclosure.

DALC-Based Bio-Ink

A composition used for forming conductive arrangements deposited on a wearable absorbent article in accordance with the present disclosure may include a dialcohol cellulose and an electrically active material. The dialcohol cellulose in the present disclosure can be in the form of DALC fibers or DALC nanofibrils. DALC fibers and nanofibrils can be prepared using methods known by a person skilled in the art. For example, DALC fibers can be obtained by oxidizing cellulose in a fiber suspension to dialdehyde cellulose followed by reduction of dialdehyde cellulose to obtain the dialcohol cellulose. If desired, DALC nanofibrils can then be obtained by microfluidization or mechanical processing of DALC fibers.

The composition may further include a plasticizer.

The electrically active material in the bio-ink refers to any material that transmits a current, for example, an electrically conductive material. In some embodiments, the composition includes between 5 wt % and 70 wt % of the electrically active material. In some embodiments, the composition includes between 10 wt % and 50 wt % of the electrically active material. In some embodiments, the composition includes 40% wt of the electrically active material.

In some embodiments, the composition includes between 30 wt % and 95 wt % of the dialcohol cellulose.

In some embodiments, the composition includes between 10 wt % and 80 wt % of the plasticizer, such as between 15 wt % and 75 wt % of the plasticizer. Alternatively, the composition may include between 1 vol % and 10 vol % of the plasticizer.

The electric conductivity of the conductive arrangement may be around 0.1 S/cm. In some embodiments, the composition has an electric conductivity of at least 0.05 S/cm, such as at least 0.1 S/cm, such as at least 0.5 S/cm, such as at least 1 S/cm.

In some embodiments, the plasticizer includes a polyol. Examples of polyol plasticizer include a glycerol, a sorbitol and an erythritol. In some embodiments, the plasticizer includes glycerol. As illustrated in the examples, glycerol, combined with DALC and PEDOT:PSS, enhanced the separation of PEDOT and PSS, thus increasing the conductivity of the composition. The addition of glycerol also enabled the composition to retain the gel nature of the ink, increased wet stability and adhesion of the ink to the substrate. Wet stability and the ability of the composition to retain moisture can prolong the shelf life of devices based on the composition of the present disclosure compared to conventional hydrogel materials.

In some embodiments, the plasticizer includes DMSO.

In some embodiments, the plasticizer includes ionic liquids. The term "ionic liquid" is commonly defined as molten salts, which are included of ions and are liquids at certain temperatures.

In some embodiments of the present disclosure, the electrically active material includes an electrically conducting polymer. It is understood that the term 'electrically conducting polymer' also may include a mixture or a complex including several polymers, which may be with or without electrically conducting properties on their own, provided that the mixture exhibits electrically conducting property. The electrically conductive polymer may, for example, include one or more polymers selected from the group consisting of polyphenylenes, polypyrenes, polyazulenes, polynaphthalenes, polyacetylenes (PAC), poly-p-phenylene vinylene (PPV), polypyrroles (PPY), polyazepines, polyanilines (PANI), polythiophenes (PT), poly-3,4-ethylenedioxythiophene (PEDOT), toluenesulfonyl (Tos) and a polystyrene sulfonates (PSS).

In some embodiments, the electrically conducting polymer includes PEDOT:PSS.

In some embodiments, the composition includes between 5 wt % and 70 wt % of the electrically conducting polymer.

In some embodiments, the composition includes between 10 wt % and 50 wt % of the electrically conducting polymer.

In some embodiments, the composition includes 40 wt % of the electrically conducting polymer.

In some embodiments, the electrically active material includes an electrically conducting carbon material. The term "electrically conducting carbon material" may include any carbon allotrope that conducts electricity. Based on the dimensional structure for electron confinement said carbons can be classified as 0D, 1D, 2D and 3D carbons. In some embodiments, the electrically conducting carbon material is selected from the group consisting of 1D carbons, 2D carbons and 3D carbons.

In some embodiments, the 3D carbon is a graphite.

In some embodiments, the 2D carbon is a graphene.

In some embodiments, the 1D carbon is a carbon nanotube.

In some embodiments, the electrically active material includes an electrically conducting 2D material. Said 2D material may be an organic or an inorganic conducting material, characterized by a 2D structure. In some embodiments, the electrically conducting 2D material is selected from the group consisting of a graphene, a MXenes and a Molybdenum disulfide ($MoS_2$).

In the following, a method of manufacturing the composition used to form conductive arrangements deposited on wearable absorbent articles in accordance with the present disclosure will be described. The method includes a step of mixing a dialcohol cellulose with an electrically active material, thus obtaining the composition.

In some embodiments, the method of manufacturing the composition further includes a subsequent step wherein the plasticizer is mixed in with the dialcohol cellulose and the electrically active material.

Processing of the Bio-Ink

The bio-ink can be further processed into an electrically conductive material. Examples of processing techniques include but not limited to extruding, printing or solution processing techniques.

In some embodiments, the composition has been applied to a wearable absorbent article by 3D-printing, 2D-printing, screen printing, stencil printing, blade-coating, melt-processing, molding, slot die coating, inkjet printing, laser printing, solution processing, vacuum filtration, solvent casting and/or paper making techniques, thus obtaining said electrically conductive material.

In some embodiments, the composition is at least partly dried before, during and/or after applying the composition.

In some embodiments, the composition is at least partly cured before, during and/or after applying the composition.

A cross-linker can be added to the composition to give it a 3D network structure. In some embodiments, the composition further includes a cross-linking agent. The cross-linking agent can be added before, during and/or after applying the composition. In some embodiments, the cross-linking agent is selected from the group consisting of ionic cross-linkers, photo cross-linkers and covalent cross-linkers.

In some embodiments, the electrically conductive material has an electrical conductivity between 0.05 S/cm and 150 S/cm, such as between 0.1 S/cm and 100 S/cm, such as 40 S/cm, such as 35 S/cm, such as 30 S/cm. In some embodiments, the electrically conductive material has an electrical conductivity of at least 0.05 S/cm, such as at least 0.1 S/cm, such as at least 0.5 S/cm, such as at least 1 S/cm, preferably it has a conductivity of at least 0.1 S/cm. However, in certain embodiment the electrical conductivity may be as high as 100, or even 150 S/cm.

A method of manufacturing an electrically conductive material to be used for a conductive arrangement in accordance with the present disclosure may include a step 3D-printing, 2D-printing, screen printing, stencil printing, blade-coating, melt-processing, molding, slot die coating, inkjet printing, laser printing, solution processing, vacuum filtration, solvent casting and/or paper making techniques.

In some embodiments, the method further includes (an) additional step(s) of adding a cross-linking agent before, during and/or after applying the composition.

Applications of the DALC Bio-Ink-Based Materials

The electrically conductive material may be use in a sensor. Such sensors may for example be capacitive sensors which can be used in numerous manners. For example, the electrically conductive material may be integrated into a material so that a change in capacitance is detected when the characteristics of the material changes. This may, for example, be the moisture content of the material, the size/dimensions of the material, and/or the deformation of the material. In other embodiments, the change in capacitance may be detected by an outside object, such as a hand or a finger that touches the sensor and thus generates a change in capacitance.

Some embodiments for a use of the electrically conductive material in an electrode.

The electrically conductive material may be used in an automotive device.

EXAMPLES

Example 1. Preparation and Assessment of the DALC-Based Conducting Inks

Materials and Methods

Materials

PEDOT:PSS (Clevios™ PH 1000, 1.3 wt %) from Heraeus. Glycerol, sodium periodate, sodium borohydride, Polyvinyl alcohol (PVA), and sulphuric acid were all purchased from Sigma Aldrich. All the chemicals were used without any further purification.

Dialcohol-modified cellulose fibers were then prepared according a previously reported method (Larsson, P. A. & Wågberg, L. Towards natural-fibre-based thermoplastic films produced by conventional papermaking. Green Chem. 18, 3324-3333 (2016)). Briefly, beaten bleached softwood kraft fibers (fines removed, fiber concentration 15 g/L) were oxidized to dialdehyde cellulose using sodium periodate (1.35 g per g of fiber). The reaction proceeded for 37 h, in the dark and at room temperature, and the pulp was washed thoroughly after completion of reaction. To determine the aldehyde content, hydroxylamine titration was used. Dialdehyde fibers were reduced to dialcohol cellulose fibers by adding sodium borohydride (0.4 g per g of fiber) and reaction carried out in 0.01 M phosphate buffer for 3 h. Subsequently, the fibers were washed thoroughly and stored at 4° C. until further use. To prepare dialcohol modified cellulose nanofibrils, dialcohol-modified cellulose fibers are microfluidized.

Preparation of DALC-Based Inks Without Plasticizer

To prepare DALC based conducting ink, dialcohol-modified cellulose fibers (degree of modification or degree of substitution 10%-50%) or dialcohol-modified cellulose nanofibrils (degree of modification 10%-50%) were mixed with PEDOT:PSS at different weight ratios, where dialcohol-modified cellulose (fibers or nanofibrils) included of at least 30 wt %, preferably between 30 and 95 wt % and PEDOT:PSS includes of at least 5 wt %, preferably between 5 and 70 wt % of the total composition of the ink.

Preparation of DALC-Based Inks with Plasticizer

Figure 4B:
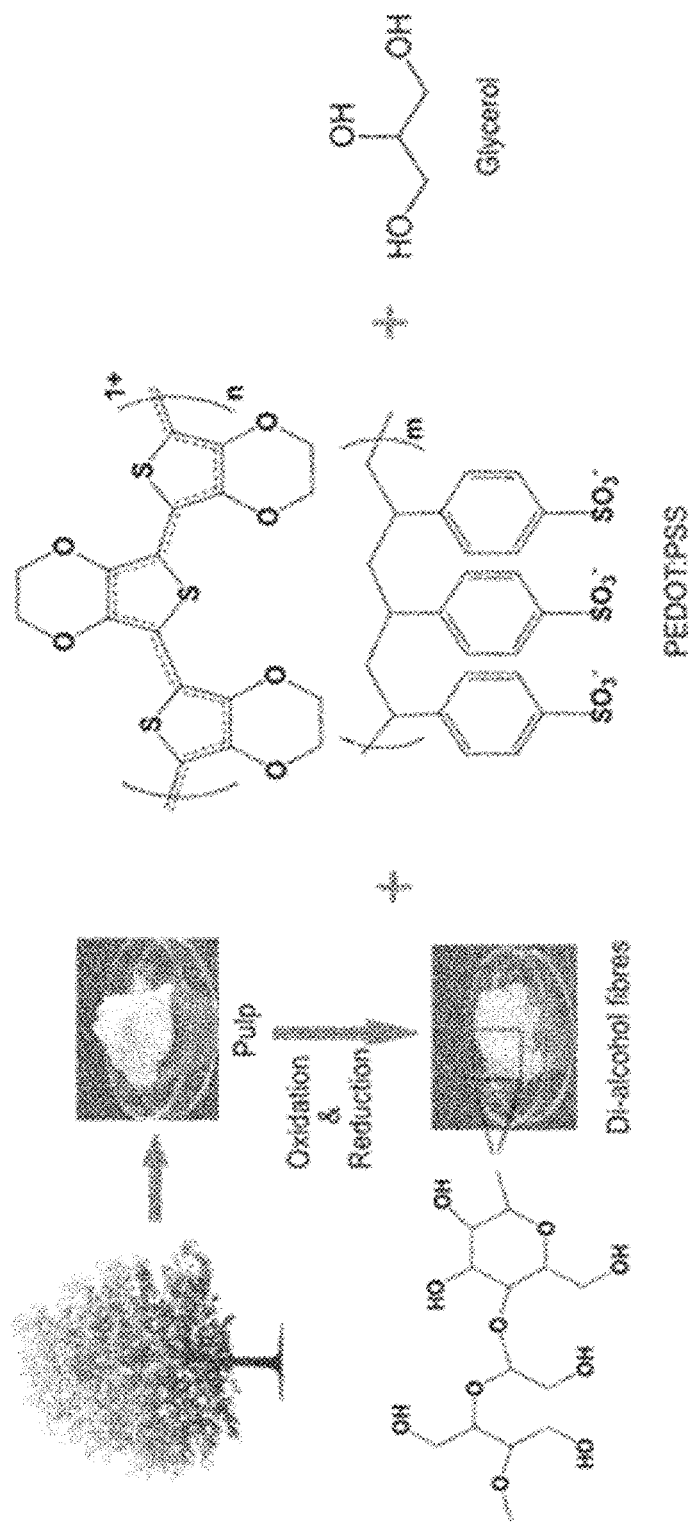
FIG. 4b shows part of a schematic process for preparing dialcohol-modified cellulose fibers for use in a conductive arrangement on a wearable absorbent article.

To prepare the inks, dialcohol-modified cellulose fibers (degree of modification or degree of substitution 10%-50%) or dialcohol modified cellulose nanofibrils (degree of modification 10%-50%) and PEDOT:PSS were mixed in different dry weight ratios where dialcohol modified cellulose (fibers or nanofibrils) included of at least 30 wt %, preferably between 30 wt % and 95 wt % and PEDOT:PSS includes of at least 5 wt %, preferably between 5 wt % and 70 wt % of the total composition of the ink. The workflow of said preparation is shown in FIG. 4b. All the inks also contained a plasticizer that included between 1 vol % and 10 vol % of the total composition (corresponds to approximately between 10 wt % and 80 wt % of the total composition). 1 vol %, 5 vol % and 10 vol % glycerol was used in preparation of the inks. Inks were placed in the fume-hood to evaporate water to achieve desired solids content.

Rheological Measurements

A DHR-2 rheometer (TA Instruments, New Castle, DE, USA) equipped with a 25 mm parallel-plate geometry (1 mm gap distance), was used to measure the rheological properties of the inks. All the measurements were performed at 25° C. Each sample was equilibrated for 10 min before analysis. The values reported are averages of three replicates. To characterize linear viscoelastic and flow properties of the inks, flow analysis was performed between 0.01 and 500 $s^{-1}$ for the inks at different PEDOT:PSS wt %, as shown in FIG. 2d, and at different solids content, as shown in FIGS. 2a and 2c. To estimate the storage (black lines) and loss (white lines) modulus, time sweep measurements were performed, and the results are shown in FIG. 5b.

SEM and EDS Measurements

Figure 7:
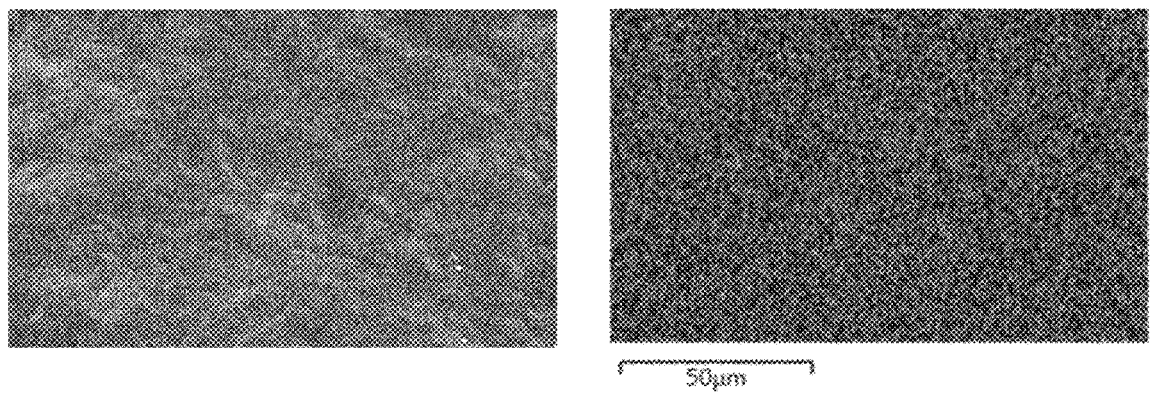
FIG. 7 shows surface (FIG. 7a) and cross section (FIG. 4b) images of a 3D printed film obtained from a composition used in a conductive arrangement deposited on a wearable absorbent article.
Figure 7:
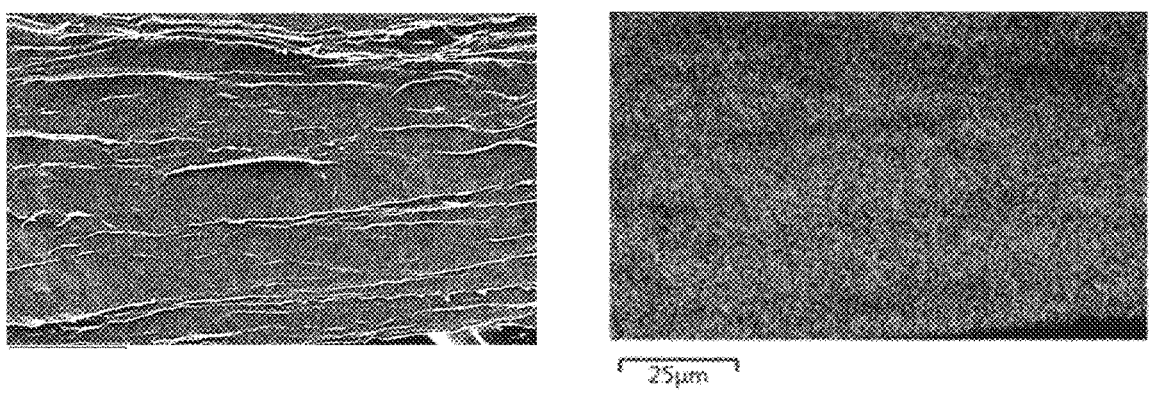

A Hitachi S-4800 Field-Emission Scanning Electron Microscope equipped with energy-dispersive X-ray spectroscopy, EDS, detector was used for studying morphology and elemental mapping. The images (A) and (B) of FIG. 7 were obtained using this setup.

Wide Angle X-Ray Scattering (WAXS)

Figure 8A:
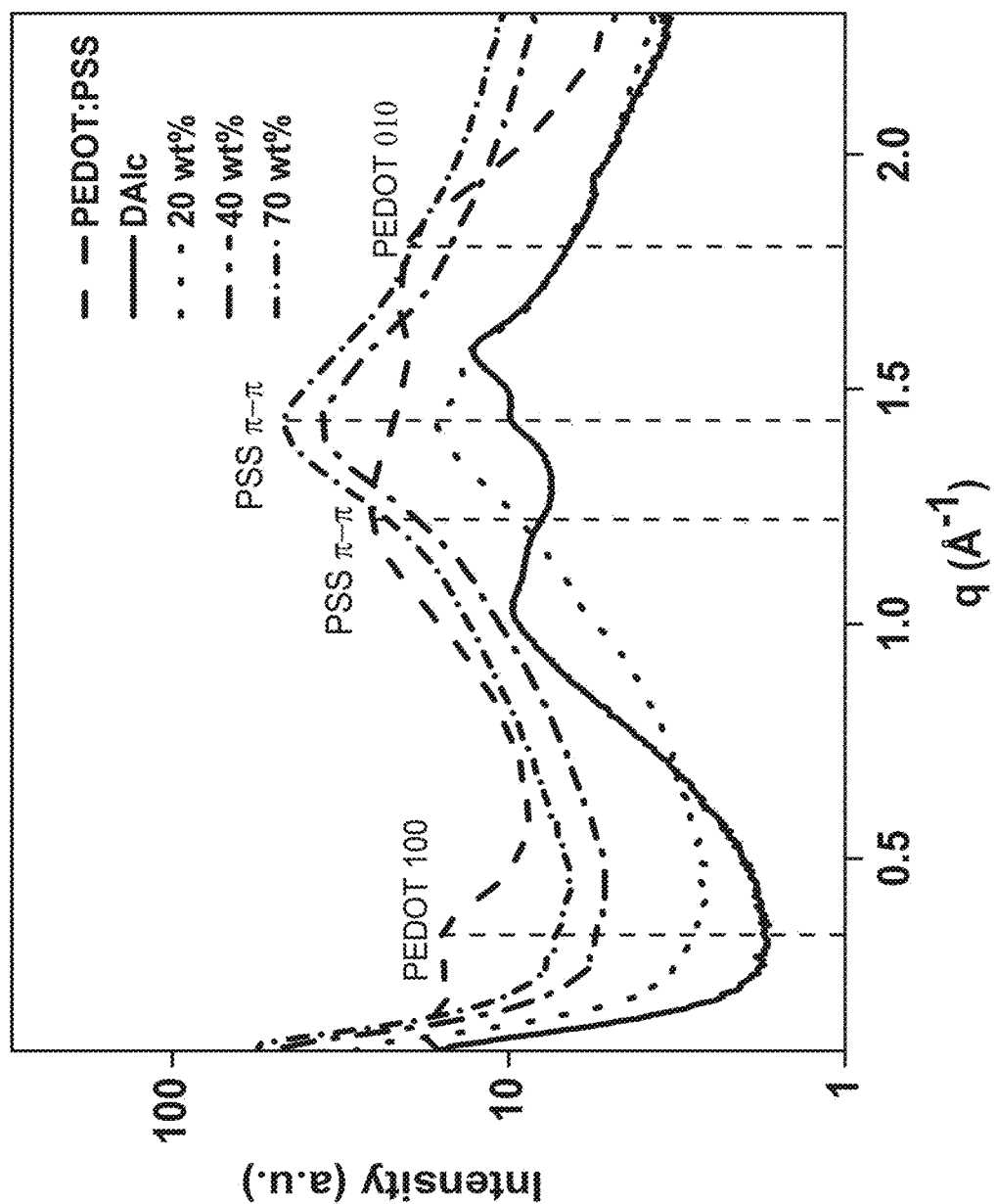
FIG. 8 shows WAXS results of embodiments of 3D printed films before (FIG. 8a) and after (FIG. 8b) washing.
Figure 8B:
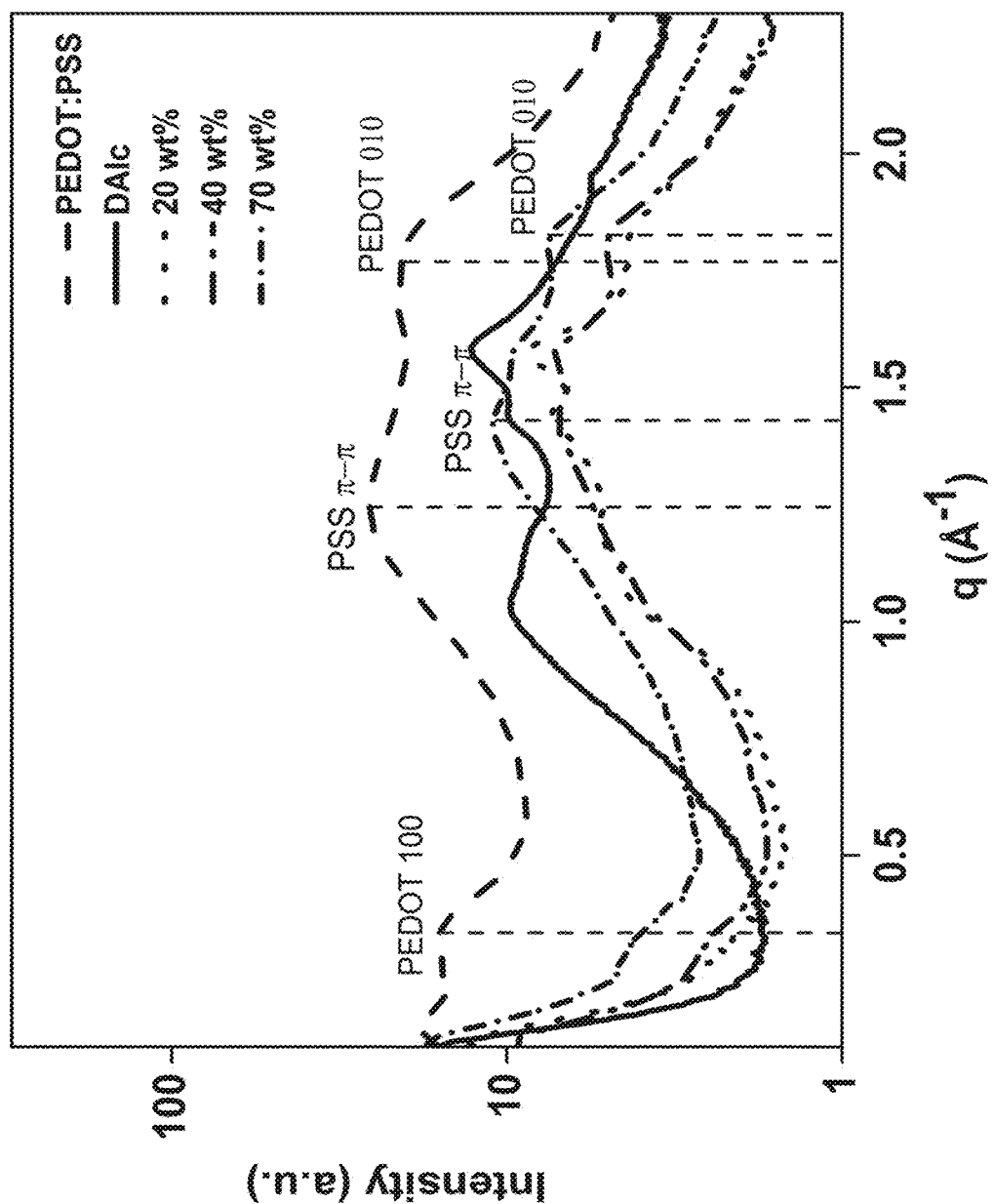

A known technique for determining the degree of crystallinity of polymers, such as the PEDOT, is wide-angle X-ray scattering (WAXS). Wide-angle X-ray scattering measurements were performed using an Anton Paar SAXSpoint 2.0 system (Anton Paar, Graz, Austria) equipped with a Microsource X-ray source (Cu Kα radiation with a wavelength 0.15418 nm) and a Dectris 2D CMOS Eiger R 1M detector. The sample-to-detector distance was 111 mm. The samples were mounted on a solid sampler (Anton Paar, Graz, Austria), mounted on a VarioStage (Anton Paar, Graz, Austria). The samples were placed under vacuum. For each sample, three frames each of 20 min duration were read from the detector. The data obtained using this setup is shown in FIGS. 8a and 8b.

Contact Angle Measurements

Figure 9:
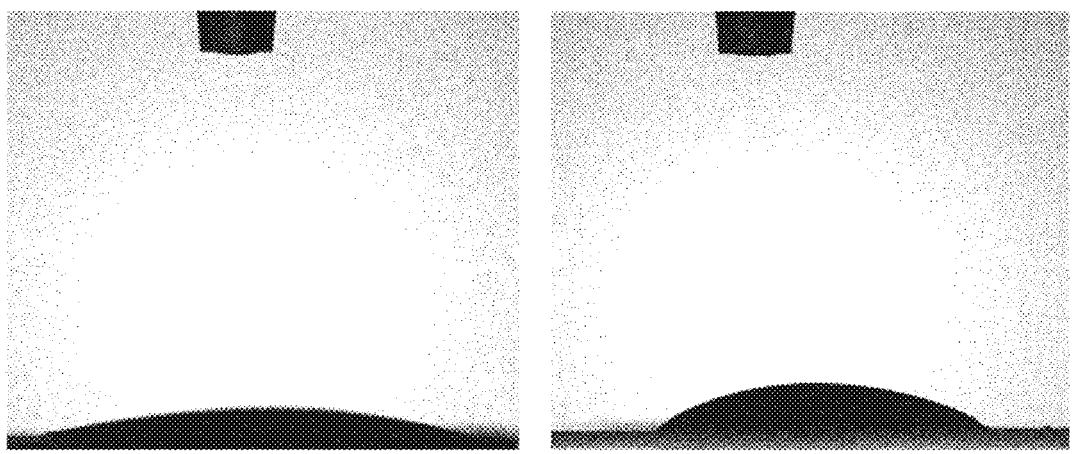
FIG. 9 compares the wetting properties of a 3D printed film using a non-DALC composition and a 3D printed film of a composition for use in a conductive arrangement deposited on a wearable absorbent article, before and after washing, respectively.
Figure 9:
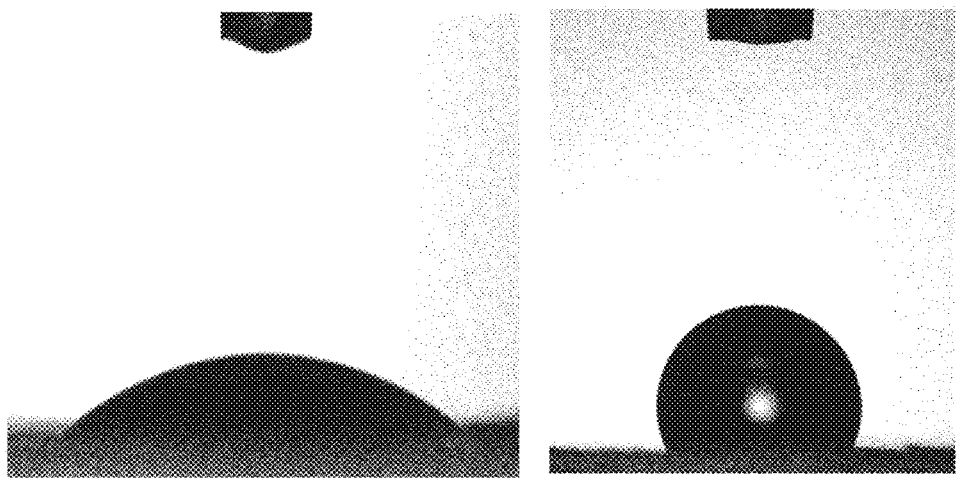
Figure 10:
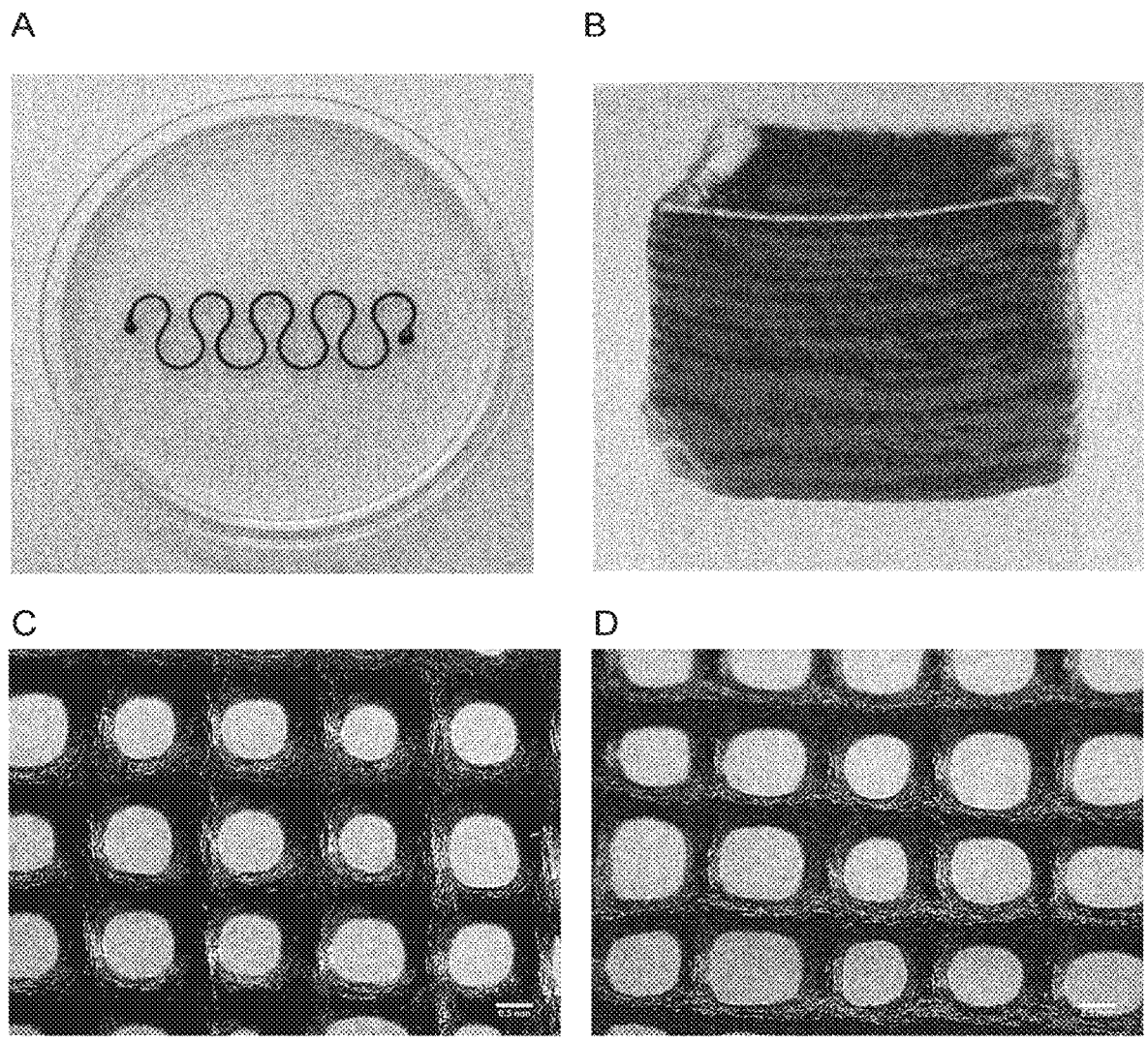
FIG. 10 shows different 3D printed structures of the compositions for use in a conductive arrangement deposited on a wearable absorbent article.

A contact angle meter (Theta lite, Biolin Scientific) was used to determine contact angle on the samples as shown in images (A) and (B) of FIG. 9.

Results

Preparation of DALC-Based Inks.

As can be understood herein it has been shown that DALC-modified cellulose can be used as a bio-based alternative to typical polymers in printable, electrically conductive inks. Although the reason is not completely understood, some similarities to e.g. PVA may be found. For example, dialcohol modified fibers haves an abundance of polar hydroxyl groups available on their surfaces. PVA is earlier known to form interpenetrated networks with PEDOT:PSS, resulting in strong, stretchable, and flexible hydrogels that can be used in, for example, energy storage devices.

The inks prepared without plasticizer showed good processability but a lower conductivity. Also, the final material was not wet stable. Hence, the plasticizer increased the conductivity of PEDOT:PSS and also helped in imparting wet stability (the reason for which is not understood fully) to the DALC/PEDOT:PSS composite.

FIGS. 5a, 5b, 5c and 5d shows a rheology analysis of the DALC/PEDOT:PSS ink at different PEDOT:PSS wt % (20 wt %, 40 wt % and 70 wt %), as well as rheology analysis of the ink (PEDOT:PSS=40 wt %) at different solids content (3-10 wt %). Inks at 6-10% solid content showed a clear shear thinning and shear yielding behavior, i.e., the ink requirements typically needed for printing. A lower solids content (1-5 wt %) of ink is usually required for printing techniques such as blade coating, stencil printing, screen printing, slot-die coating or solution processing. The inks with solids contents of 6-8 wt % were used for 3D printing in the subsequent examples.

The inks showed a gel-like behavior at solids content above 3 wt %. Atomic force microscopy (AFM) image of dry samples showed that PEDOT:PSS particles were organized on DALC surface in a pearl-necklace-like morphology, as seen in FIG. 3. Hence, it can form an entangled network of PEDOT:PSS covered fibers providing a gel-like character.

Interaction Between DALC Fibers and PEDOT:PSS

To assess the distribution of PEDOT:PSS in DALC/PEDOT:PSS composites, scanning electron microscopy (SEM) images and sulfur mapping images of 3D-printed samples were collected. They showed a surface and layered cross-section, as shown in FIGS. 7a and 7b, covered with PEDOT:PSS particles where individual fibers cannot be identified as the DALC fibers have film forming properties. Hence, good conductivity can be achieved owing to a homogeneous adsorption of PEDOT:PSS particles on both exterior and inner surfaces of the fibers due to the excellent film forming properties of DALC fibers.

An important factor for a good conductivity is removal of free PSS from PEDOT:PSS and thereby a better packing of PEDOT crystallites. As can be seen in FIGS. 8a and 8b, WAXS showed an intense PSS peak that shifted from 1.3 $Å^{-1}$ in pure PEDOT:PSS to 1.4 $Å^{-1}$ in 3D printed films (d-spacing 0.51 nm to 0.44 nm), showing a reduction in stacking distance between PSS crystallites. However, the PEDOT 010 and the PEDOT 100 peak responsible for π-π stacking of PEDOT crystallites are absent (FIG. 5a). On the other hand, after washing of the 3D-printed films in water, these PEDOT peaks appeared, as well as significant concomitant reduced intensity of the PSS peak (FIG. 8b). Furthermore, the PEDOT 010 peak typically assigned for edge-on orientation of PEDOT crystallites, shifted from a q-value of 1.73 $Å^{-1}$ in pure PEDOT:PSS to 1.82 $Å^{-1}$ in 3D-printed samples, leading to a decreased stacking distance (from 0.36 nm to 0.34 nm). However, only a very weak PEDOT 100 peak, indicative of face-on orientation of PEDOT crystallites, appeared in the 3D-printed films. Therefore, based on WAXS, it can be suggested that DALC fibers are not only acting as a template for PEDOT:PSS particles but they are also inducing a PSS phase separation required for an increased conductivity in PEDOT:PSS (Ouyang et. Al., 2015). In addition, close packing of PEDOT crystallites in edge-on orientation is favored, which has been shown to be responsible for high conductivity of PEDOT:PSS. The analysis of morphology and x-ray scattering showed that DALC fibers may induce a similar crystallization in PEDOT:PSS as ethylene glycol or other secondary dopants.

Contact angle measurements, as shown in FIGS. 9a and 9b, of the printed DALC/PEDOT:PSS films showed the increase in contact angle from 18 degrees for as printed and dried films to 121 degrees after washing these films. This shows that the surface changed from hydrophilic to hydrophobic due to enrichment in PEDOT. Whereas, in pure PEDOT:PSS/glycerol films, the contact angle changed from 14.5 degree to 38 degrees, which is indeed not as significant. It implies that the surface is enriched with more PEDOT domains (as PEDOT is more hydrophobic) and PSS removal after washing. This effect is more apparent in DALC/PEDOT:PSS/glycerol samples than pure PEDOT:PSS/glycerol samples. Therefore, dialcohol cellulose is important to induce a larger phase separation of PEDOT:PSS.

In other words, conducting inks based on dialcohol-modified cellulose fibers and PEDOT:PSS that exhibit wet stability were produced. DALC fibers acts as a template for PEDOT:PSS particles and helps in phase separation of PSS and PEDOT that leads to high conductivity in printed inks even with low content of PEDOT:PSS. The use of modified-cellulose-fibers also eliminates the need for cellulose nanofibrils, which has higher embedded energy, often used for bio-based electronics.

Example 2. Processing of Inks and Electrical Characterization

A direct-ink-writing 3D bio-printer was used to print different 2D and 3D patterns as shown in FIGS. 10a-10d. Although a 3D bio-printer is used, the inks can be printed with other printing techniques as well. These can also be processed using melt extrusion, solution processing techniques as well as paper making techniques.

Materials and Methods

An Inkredible 3D bio-printer (Cellink®) was used for printing. Inks were transferred to a syringe, centrifuged for 30 s to remove any air bubbles introduced during mixing, and printed with high-precision conical nozzles (20 G, 25 G and 27 G, Cellink®). The print head speed and print pressure were manually adjusted for each ink composition. The printed samples were dried at 60° C. in oven overnight.

Electrical and Electrochemical Measurements

Two-probe conductivity test was performed using a Keithley 2410 source meter. Samples were cut in rectangles with dimensions of 2 cm×0.5 cm×(thickness) and voltage was recorded at constant current. Resistance was calculated from the slope of the I-V curve. The following formula was used to calculate the conductivity:

$$\rho = (R \times w \times t)/L$$

$$\sigma = 1/\rho$$

where $\rho$ is the resistivity, R is the resistance of the sample, w is the width, t is the thickness, L is the distance between two electrodes and $\sigma$ is the conductivity.

Cyclic voltametery and galvanostatic charge/discharge measurements were performed with a three electrode setup using BioLogic VSP potentiostat. The setup consisted of: Ag/AgCl (BASi®, 3M NaCl) reference electrode, a platinum counter electrode and 3D printed sample mounted on a platinum wire as a working electrode; dipped in 1 M sulphuric acid as electrolyte. The open circuit potential was recorded before starting each measurement. The specific capacitance of the material was calculated from discharge cycle as follows:

$$C = (It)/(m\Delta V)$$

where, I is the discharge current, t is the discharge time, $\Delta V$ is the voltage window and m is the mass of PEDOT in the sample.

Mass of PEDOT in the measured sample was calculated as follows:

A rectangular piece (20 mm×5 mm) of 3D-printed DALC/PEDOT:PSS sample was weighed (MO) and then dipped in 1 M H2SO4 overnight and washed thoroughly with milli-q water afterwards. The sample was left to dry in ambient conditions and the mass of dried sample was again measured (Mf). Since, the sample lost glycerol and some PSS present in the sample (the residual electrolyte was transparent after sample dipping), the final weight includes of only cellulose fibers and PEDOT:PSS.

Mass of cellulose and PEDOT:PSS in printed sample=Mf

Mass of PEDOT:PSS in the sample=0.4*Mf, calculated based on initial ratio (DALC/PEDOT:PSS) of the ink Mass of PEDOT in the sample=1/3.5*(0.4*Mf), since the original ratio of PEDOT:PSS (as purchased) is 1:2.5 (neglecting the loss of PSS)

Results

Figure 11:
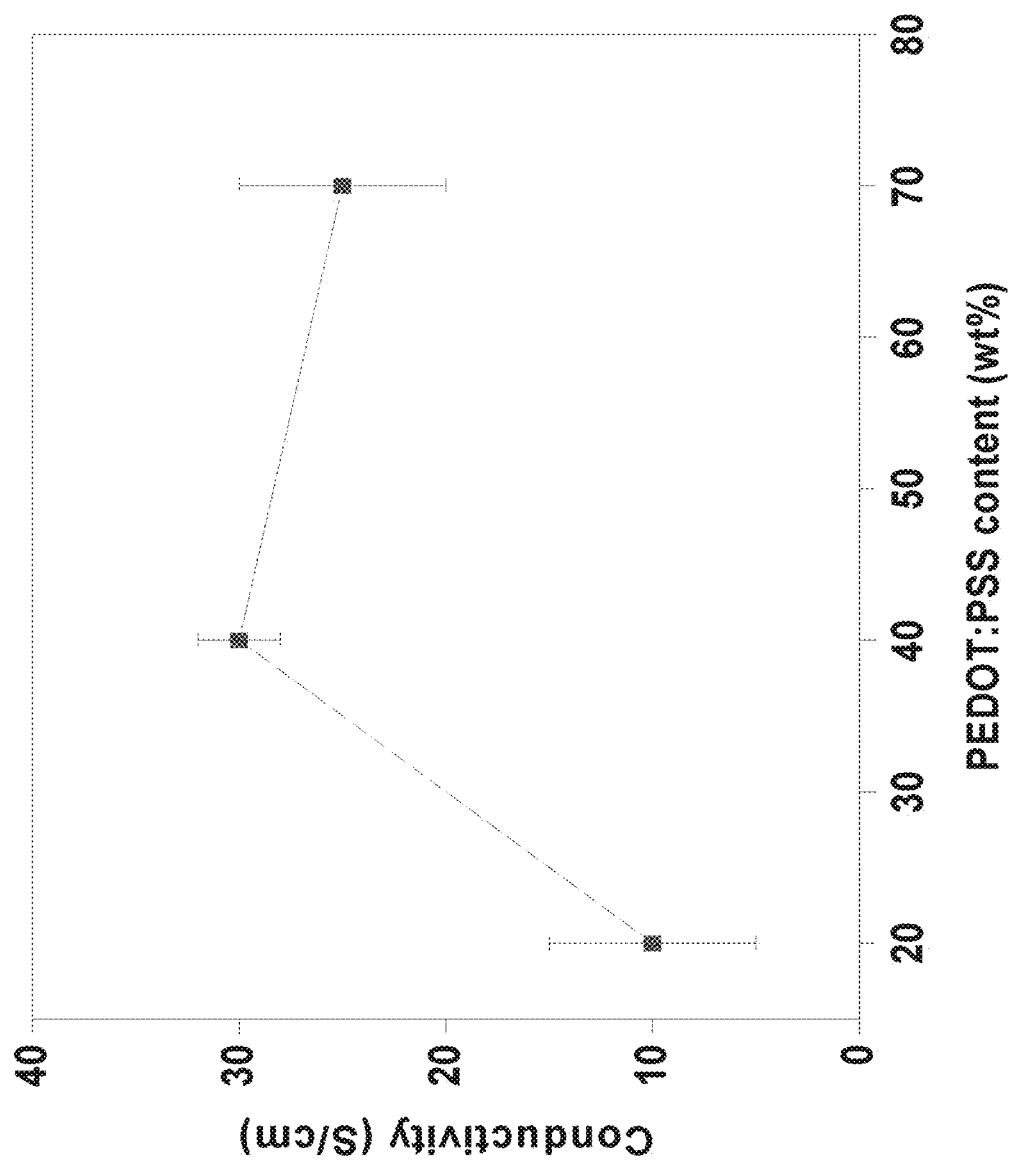
FIG. 11 shows the electrical conductivity of a 3D gel printed using an embodiment of a composition for use in a conductive arrangement deposited on a wearable absorbent article.
Figure 12:
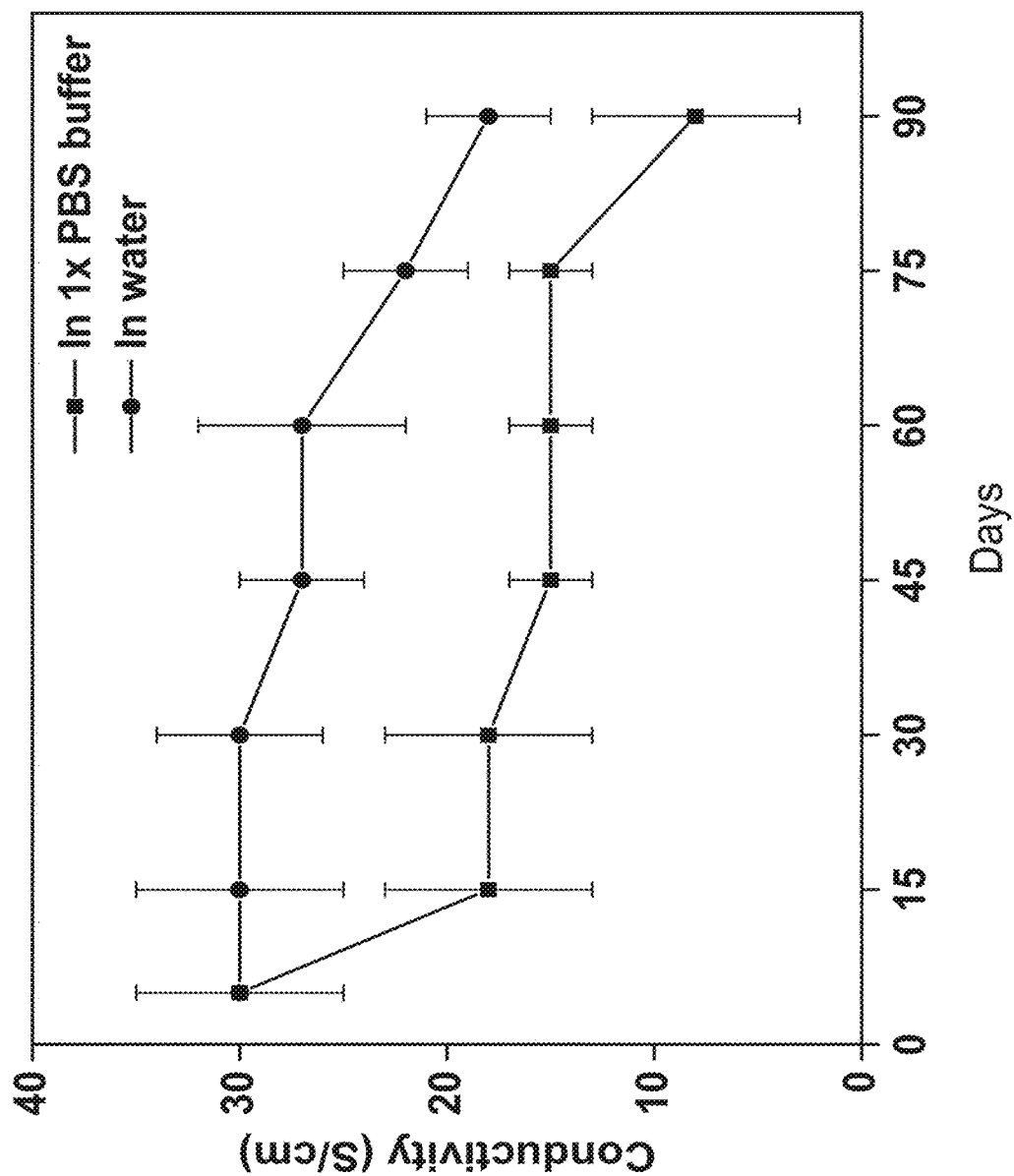
FIG. 12 shows electrical conductivity measurements of other 3D printed films soaked in water or phosphate buffer solution (PBS) using a composition for use in a conductive arrangement deposited on a wearable absorbent article.
Figure 13:
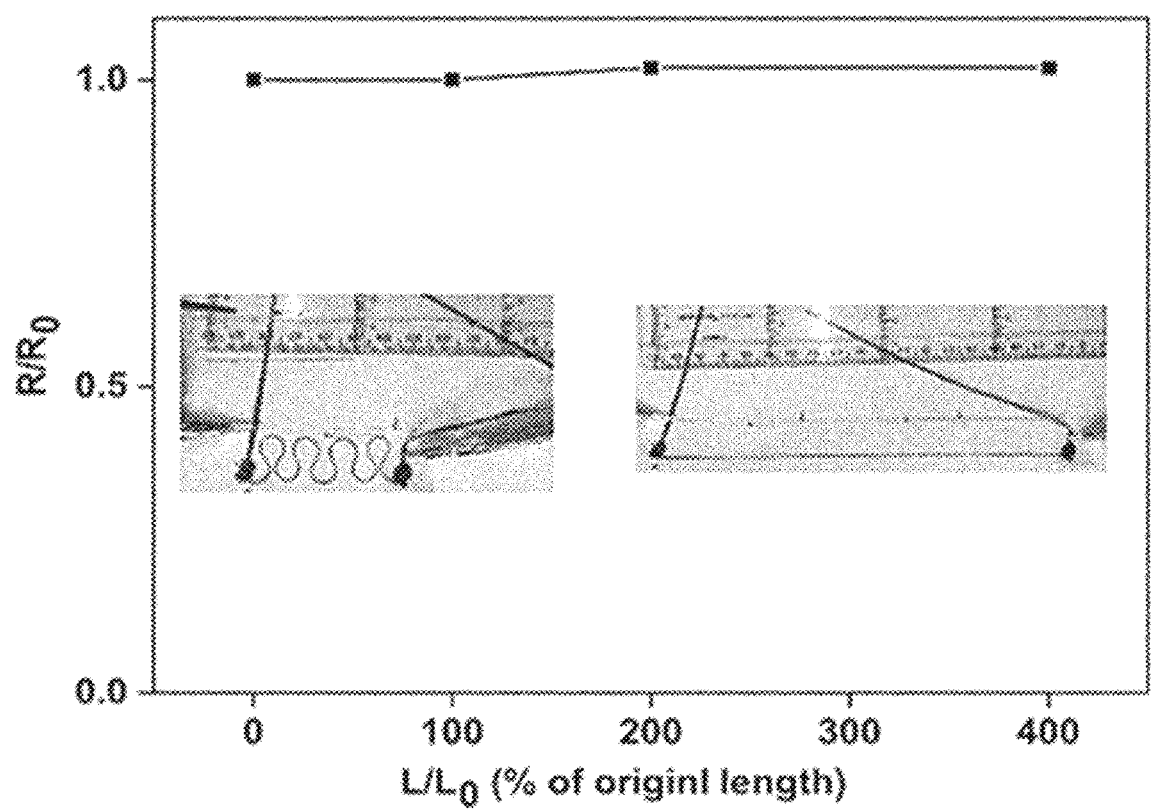
Figure 13:
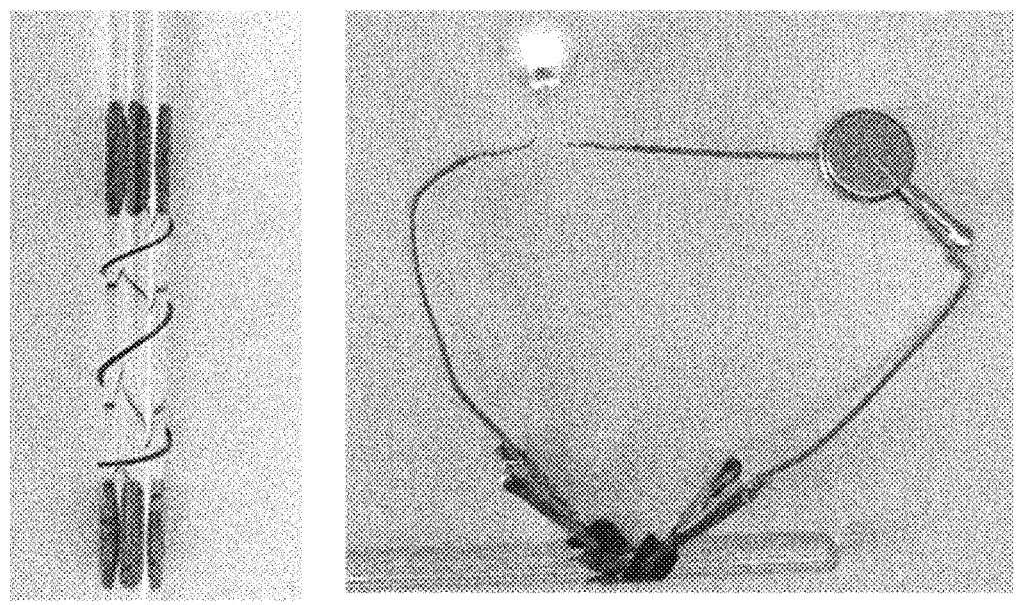

The 3D-printed gels had a conductivity of 30±3 S/cm. The conductivity increased with PEDOT:PSS content to level off at a PEDOT:PSS content of 40 wt %, as shown in FIG. 11. This indicates a saturation threshold in 3D-printed samples, with a conductivity of ~10 S/cm even at 20 wt % PEDOT:PSS, which is good enough for bio-electronic applications. To the best of our knowledge, it is the first demonstration of such good conductivity values obtained for a 3D-printed, cellulose-fiber-based PEDOT:PSS ink where the conducting material only accounts for 20% of the total mass. Furthermore, the printed materials were stable in water and physiological solutions for at least 75 days without significant loss in conductivity, as seen in FIG. 12. A rapid conductivity drop in PBS in comparison to water could be attributed to de-doping of PEDOT:PSS in salt solution. The 3D-printed patterns are bendable, and elastic with conductivity retention of 99%, here demonstrated by a still glowing LED-light after stretching the printed serpentine pattern (FIGS. 13a and 13b).

Electrochemical Performances

Figure 14:
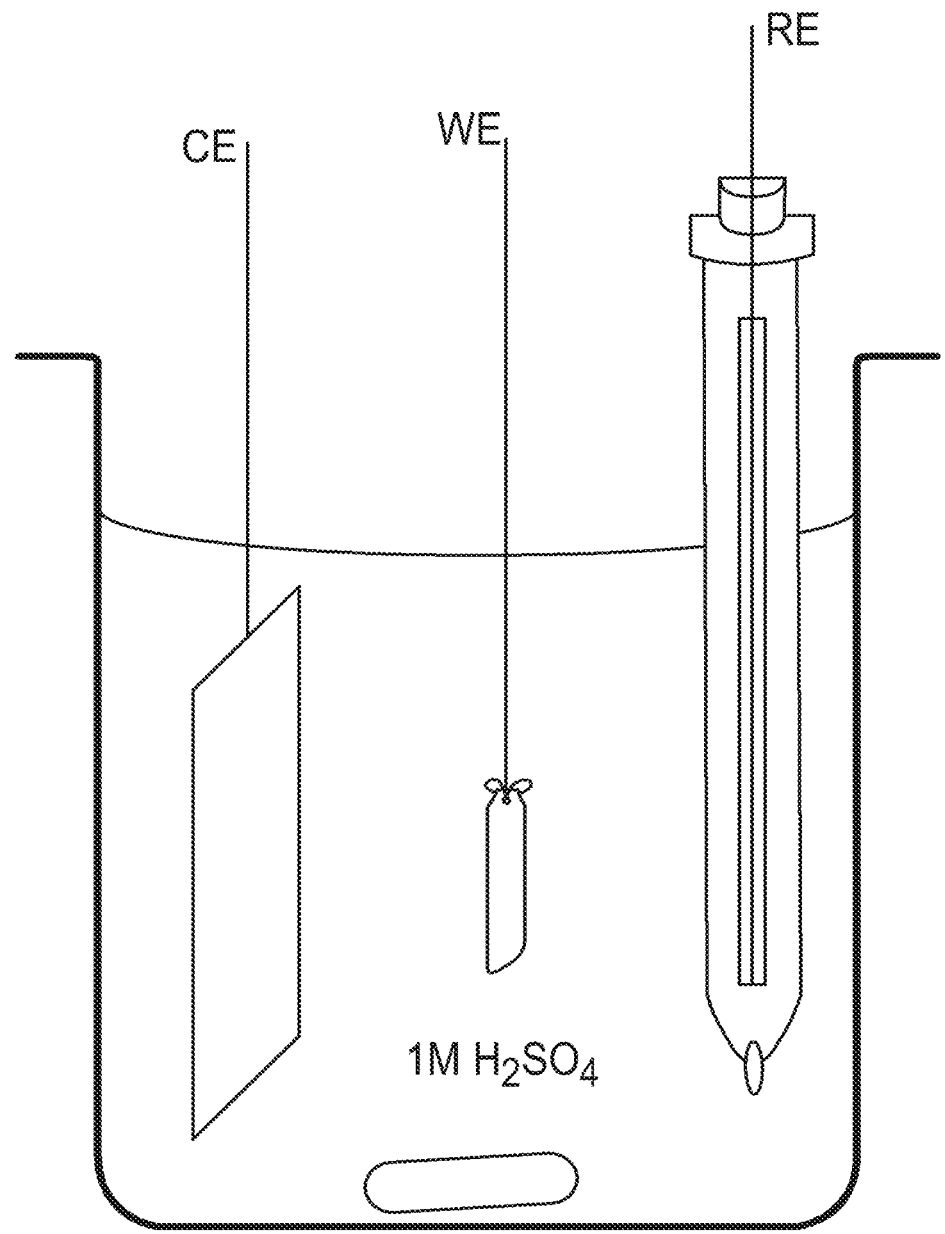
FIG. 14 shows a schematic test setup including a reference electrode, RE (Ag/AgCl); counter electrode, CE (Pt electrode); and working electrode, WE (3D printed sample mounted on Pt wire) for electrochemical testing a 3D sample printed using a composition for use in a conductive arrangement deposited on a wearable absorbent article.
Figure 15:
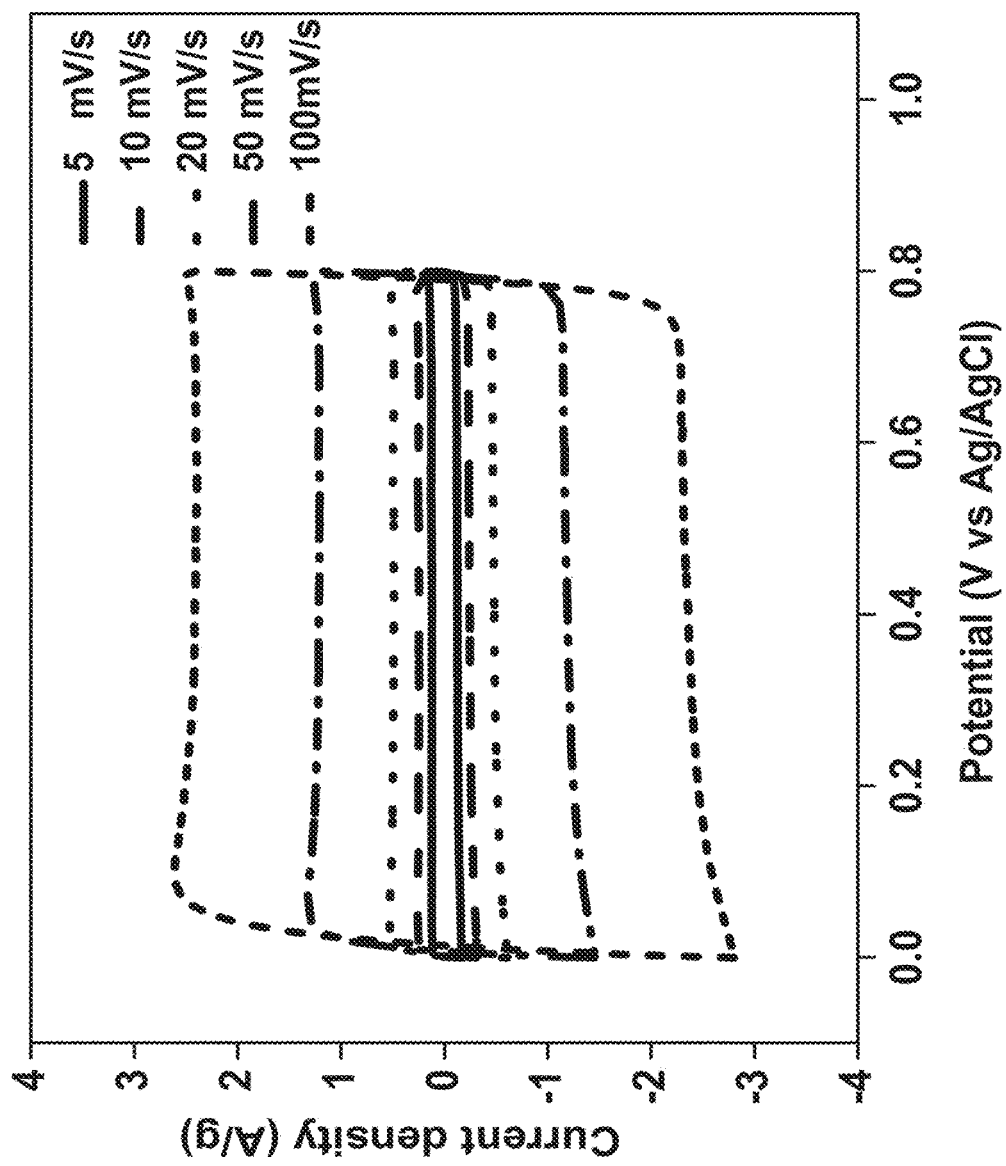
FIG. 15 shows measurements obtained from the test setup of FIG. 14.
Figure 16:
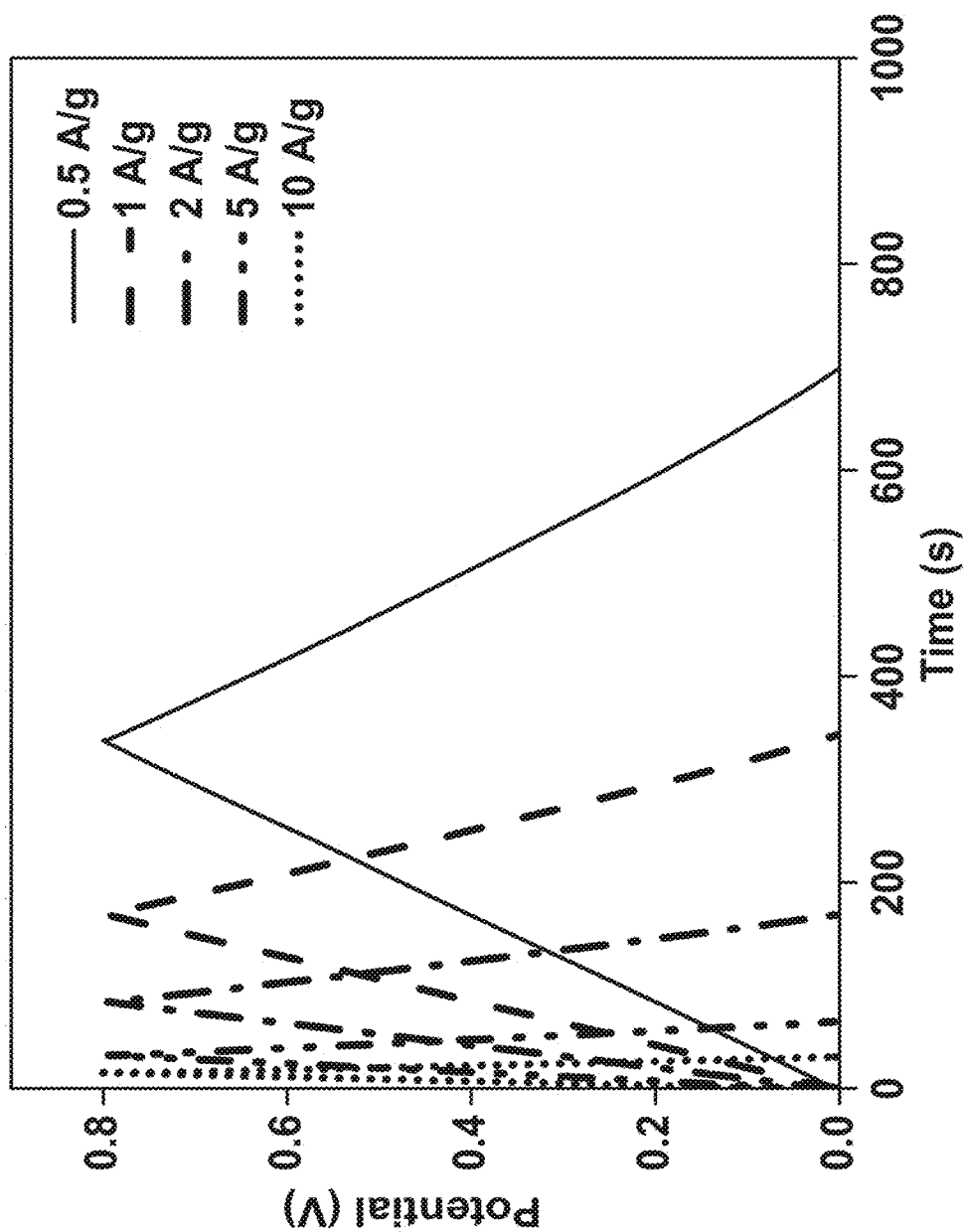
FIG. 16 shows measurements obtained from the test setup of FIG. 14.
Figure 17:
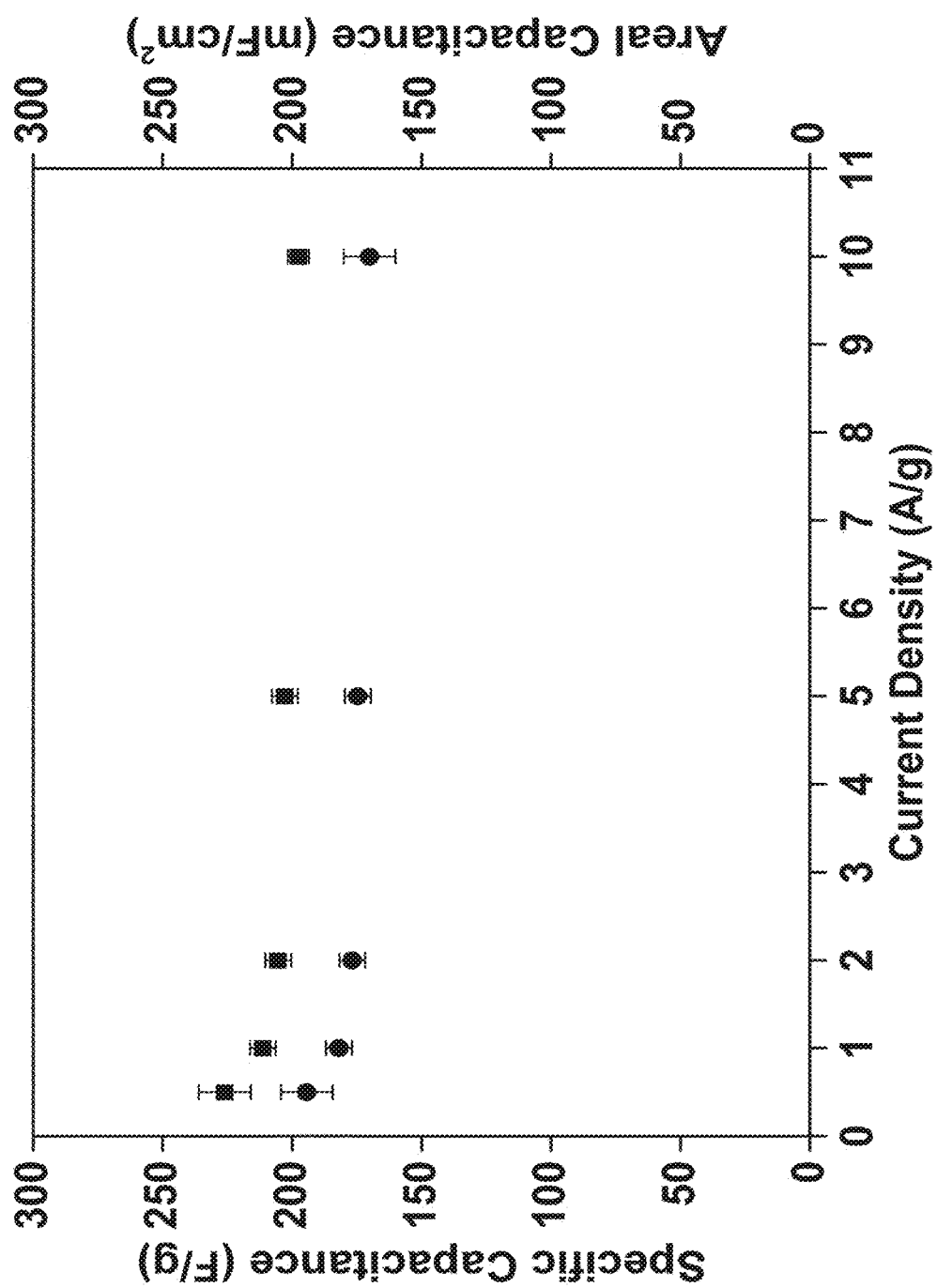
FIG. 17 shows measurements obtained from the test setup of FIG. 14.

To demonstrate the potential of the developed 3D-printable conducting inks in energy storage applications, the electrochemical performance was analysed using a three-electrode setup (FIG. 14). Cyclic voltametery (CV) for a material containing 40 wt % PEDOT:PSS showed an ideal supercapacitive behavior, maintaining a quasi-rectangular shape even at high scan rates of 100 mV/s (FIG. 15), i.e., the typical response from electrical double-layer capacitor. The galvanostatic charge-discharge (GCD) curves are triangular in shape without significant potential drop (FIG. 16), showing an efficient charge storage ability due to the high conductivity of the printed working electrode. The gravimetric discharge capacitance is as high as 197 F/g (normalized with PEDOT mass) and the areal capacitance is 170 mF/cm2 even at 10 A/g (FIG. 17). The capacity normalized with respect to the mass of the entire electrode is listed in Table 1. As can be seen, 3D-printed samples are approaching the theoretical specific capacitance of 210 F/g (Snook et. al., 2011) for PEDOT, despite the fact that only 40% of 3D printable ink is PEDOT:PSS. The specific capacitance at current density of 1 A/g increases from 26 F/g to 211 F/g when the PEDOT:PSS content is increased from 20 wt % to 40 wt %, but then decreased to 158 F/g if the PEDOT:PSS content was further increased to 70 wt % (Table 2), i.e. following the same trend as the conductivity values. Again showing that a good electrically conductive network is formed even at low PEDOT:PSS contents.

Figure 18:
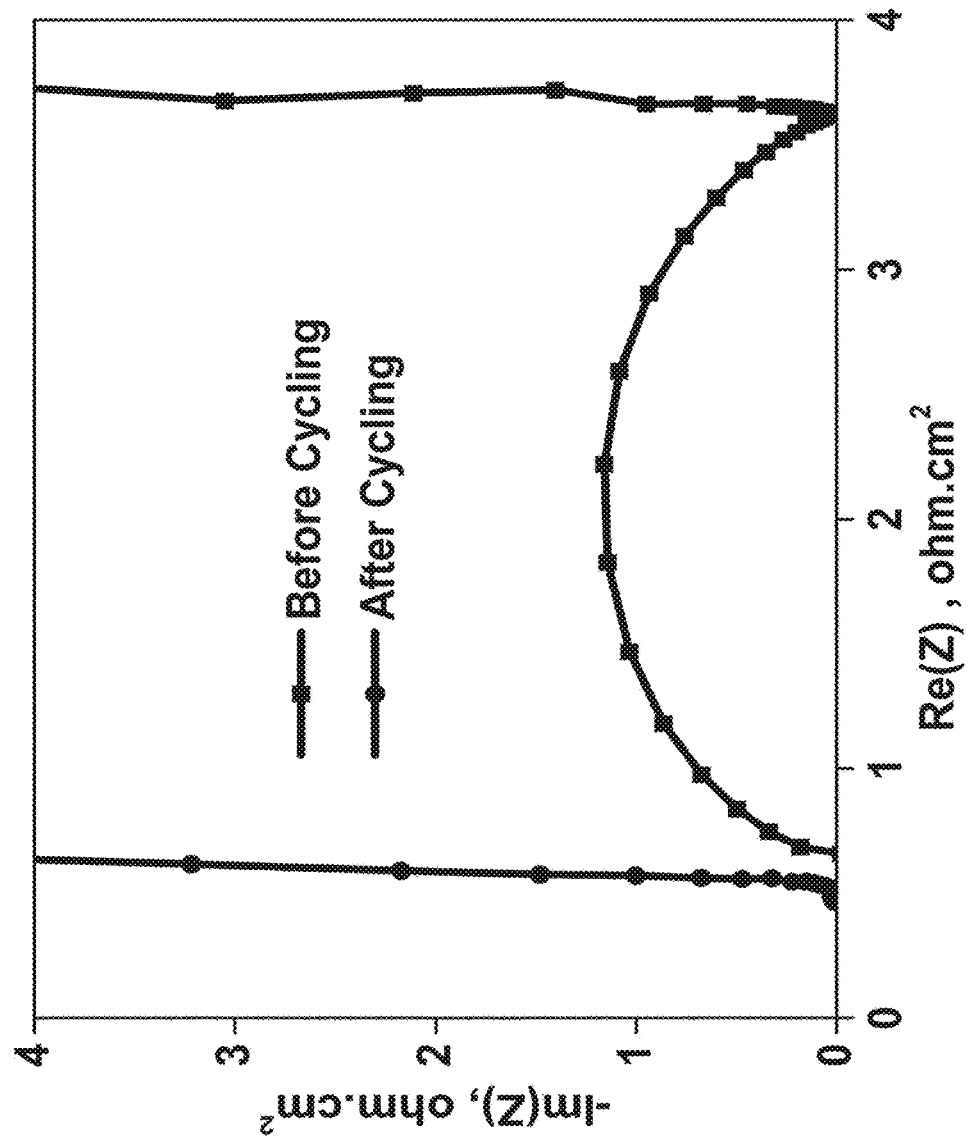
FIG. 18 shows measurements obtained from the test setup of FIG. 14.
Figure 19:
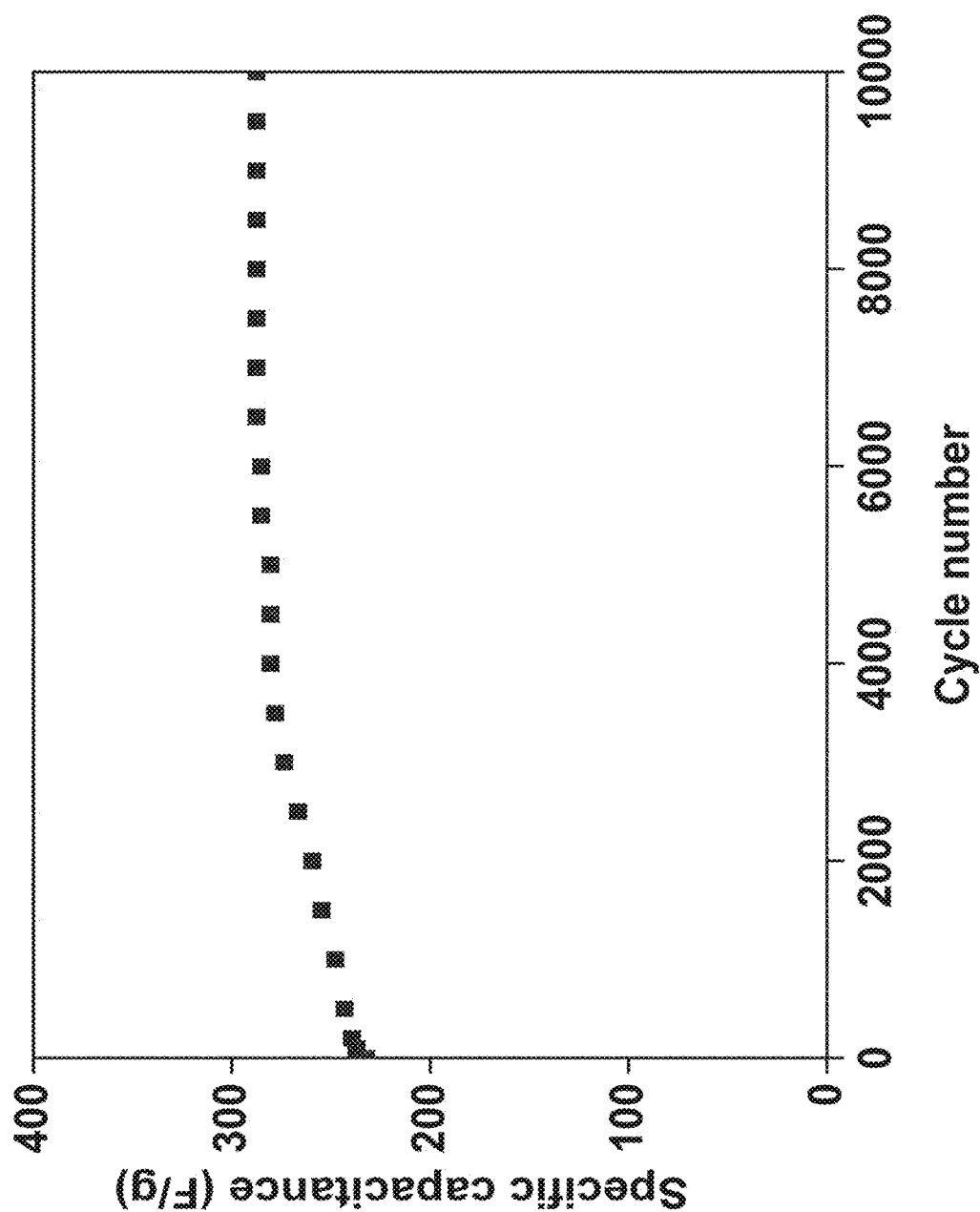
FIG. 19 shows measurements obtained from the test setup of FIG. 14.

The ion transport and charge transfer kinetics were studied using electrochemical impedance spectroscopy (EIS) within a frequency range of 10 MHz to 1 MHz. Before initiating any charge/discharge cycling, the Nyquist plot (FIG. 18) shows a small intercept on the real impedance axis in the high-frequency range, 0.7 $\Omega \times cm^2$, indicating that the printed electrode had a very low intrinsic resistance. The semicircle at the high-to-medium frequency range indicates charge-transfer resistance. The semicircle disappears after 10 000 charge-discharge cycles, indicating that the charge transfer at the electrode/electrolyte interface is improved during the cycling. This good charge transfer is also the reason why an increased (from 230 to 280 F/g) capacitance was observed after 10 000 cycles (FIG. 19).

TABLE 1

Specific capacitance and current density values calculated by considering different active mass components

| Active mass components | Specific Capacitance (F/g) | Current density (A/g) |
|---|---|---|
| PEDOT | 211 | 1 |
| PEDOT:PSS | 61 | 0.3 |
| PEDOT:PSS + DALC + glycerol | 30 | 0.1 |

TABLE 2

Specific capacitance values for 3D printed samples with different PEDOT:PSS content at 1A/g

| PEDOT:PSS content (by weight) | Specific Capacitance (F/g) |
|---|---|
| 20 | 26 |
| 40 | 211 |
| 70 | 158 |

Conclusion 3D printed samples show comparable electrochemical performance as state of the art bio-based PEDOT:PSS supercapacitors that either use secondary doping such as acid treatment for doping PEDOT:PSS or a mixture of PEDOT:PSS and other redox active molecules.

The vertical tails of the Nyquist plots (FIG. 18) in the low-frequency range suggest the diffusive resistance of the electrode is very low, benefitting from the gel-like electrode structure.

Example 3. Wearable Bio-Electronic Devices

Materials and Methods

For electrical and electrochemical measurements please refer to Materials and methods in Example 2.

EC-12 Tests and ECG and EMG Measurements

EC-12 tests were performed at Beneli AB, Sweden in gel-gel configuration using SEAM ECG Electrode Test Platform (QC Integrated, Ontario, Canada).

To perform the ECG recordings, a reference electrode was placed on the abdomen of a person and then one electrode (either gel or printed PEDOT) on each of the person's index fingers. To record the activity generated by the opening and closing of the hand, a reference electrode was placed on the elbow and two printed PEDOT electrodes were placed on opposite sides of the forearm. The signals produced by the hand signs were recorded using the same configuration and adding a third electrode in between the other two. The electrical signals were registered using a RHD2132 amplifier (INTAN Technologies, USA) on a custom PCB board. The output of the amplifier was connected to an integration module containing a Spartan-6 FPGA (model XEM6010-LX45, Opal Kelly Inc., USA) from which it was collected by a laptop via a USB connection using the RHX Data Acquisition Software (Intan Technologies, USA). The signals were recorded at a rate of 20 kS/s using different frequency ranges on each case: 1 to 100 Hz for ECG and 0.1 to 1 kHz for EMG. The acquired digital signals were processed offline with the aid of Python programming.

The power line interference on the signals was removed by applying second-order IIR digital filters with stop frequencies at 50, 100, 150, 200, 300 and 400 Hz. Fourth-order high- and low-pass Butterworth filters were applied at 1 KHz and 1 Hz respectively to restrict the signals to the desired frequency bands. The P-QRS-T complexes on the ECG signal were detected as the 1 s windows around peaks with a height larger than 5 times the standard deviation of the signal. For the hand-sign EMG monitoring, first the signals from all three electrodes were merged to detect windows of events. The merged signal was squared, smoothed using a running average with a window of 1000 samples and normalized. The 1-sample differential was calculated on the smoothed, normalized signal. A threshold of 0.07 was used on the differential to distinguish windows of events with EMG activity from the background. On each event-window, the power of the signal of each electrode was computed and normalized by the power of the added signals.

Results

Figure 20:
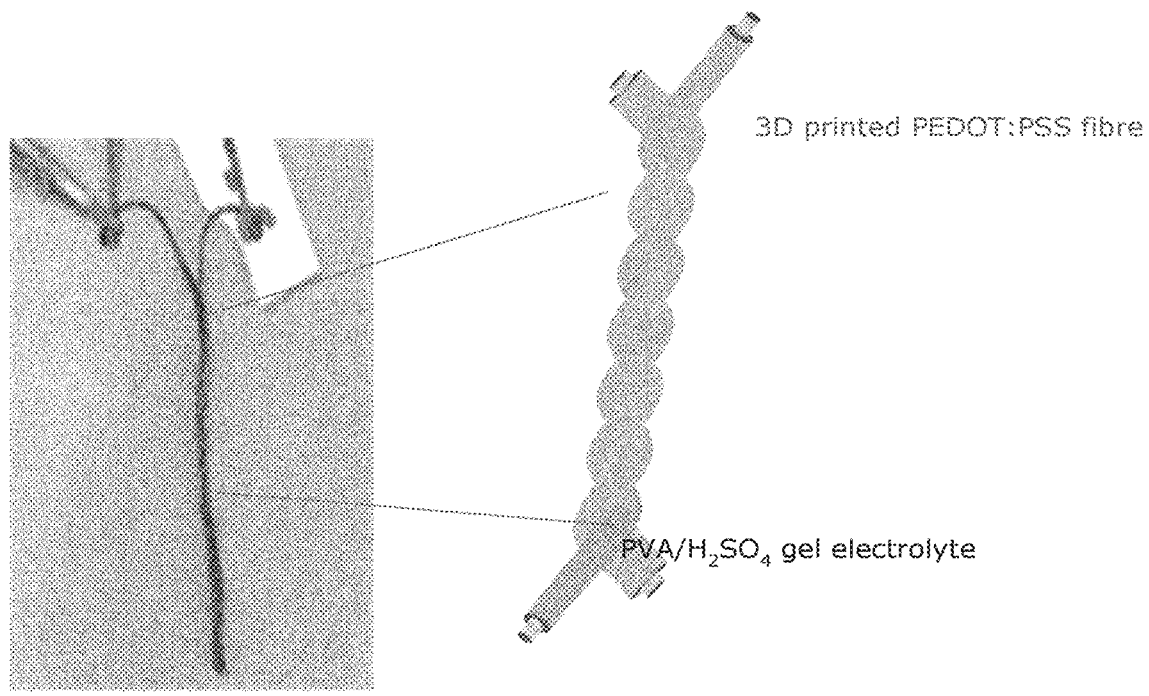
FIG. 20 shows an embodiment of a fabricated supercapacitor device including an embodiment of an extruded composition
Figure 21:
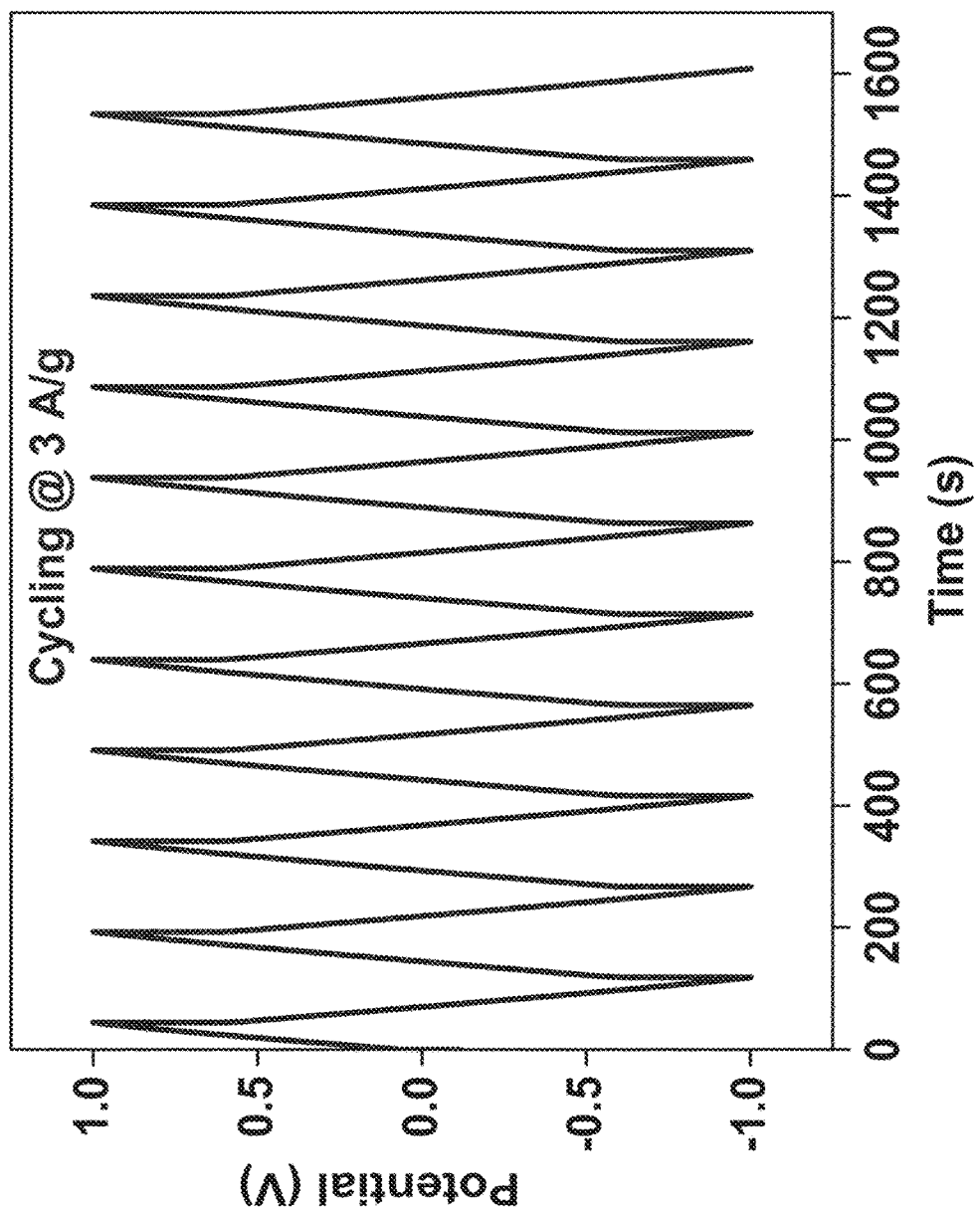
FIG. 21 shows galvanostatic charge/discharge curves of the device of FIG. 20.

Owing to the stretchability, flexibility and good electrochemical behavior of the 3D-printed electrodes, it was possible to fabricate a supercapacitor device by twisting two extruded filaments coated with gel electrolyte (FIG. 20). The two-electrode device shows a discharge capacitance of 123 F/g and a good cyclability at 3 A/g (FIG. 21), demonstrating a potential where extruded fibers can be weaved as a textile, for wearable energy storage devices.

Furthermore, to assess the potential of 3D printed electrodes in electrocardiogramonitoring, (ANSI:AAMI EC12: 2000) standard tests for disposable ECG electrodes in electrode-electrode configuration were performed. Different parameters measured for three different PEDOT:PSS contents are summarized in Table 3a and b. Besides default parameters such as AC impedance, DC offset voltage and noise, defibrillation discharge was measured, which determines the electrode's ability to measure ECG after a defibrillation event.

Figure 22:
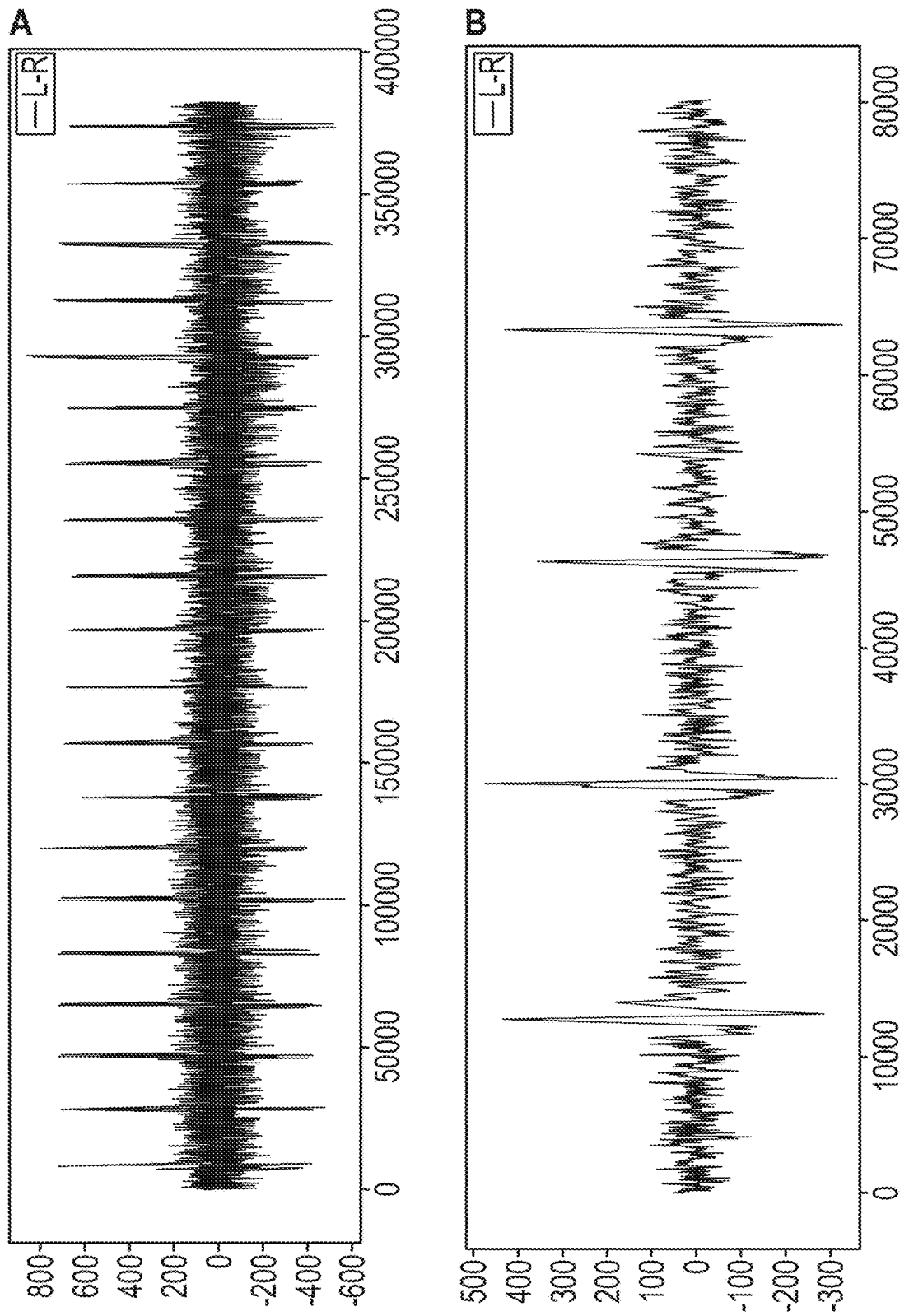
FIG. 22 shows ECG measurements from the wearable electrode device.

As can be seen from Table 3, even with as little as 20 wt % of PEDOT:PSS, the AC impedance, the noise level and the defibrillation discharge had better values than recommended by the standard. To further test and demonstrate the material's applicability in ECG monitoring devices, 3D-printed electrodes were tested to record ECG signals. A standard 3-lead ECG shows good ECG signal with clear P-QRS peaks (FIG. 22a and FIG. 22b).

TABLE 3a

EC-12 test results for 3D printed electrodes

| Measurement Parameters | Dimensions of electrodes (mm) | AC impedance (Ω) | DC offset voltage (mV) | References |
|---|---|---|---|---|
| Standard ANSI/AAMI EC12-2000 | | 10 KΩ | <100 | Tsukada et al., 2019 |
| PEDOT: PSS/DALC (20/80) | 17 × 7 | 28.8 ± 5.0 | 0.4 ± 0.2 | This work |
| PEDOT: PSS/DALC (40/60) | 17 × 7 | 34.5 ± 11.0 | 0.4 ± 0.3 | This work |
| PEDOT: PSS/DALC (70/30) | 17 × 7 | 32.8 ± 8.0 | 0.4 ± 0.3 | This work |
| Ag/AgCl with adhesive gel | 18 × 35 | 33 KΩ | — | Tsukada et al., 2012 |

TABLE 3a-continued

EC-12 test results for 3D printed electrodes

| Measurement Parameters | Dimensions of electrodes (mm) | AC impedance (Ω) | DC offset voltage (mV) | References |
|---|---|---|---|---|
| PEDOT:PSS silk glycerol thread | 7 × 12 | 0.2 KΩ | — | Tsukada et al., 2012 |
| Hitoe ® electrode (polyester nanofibre yarn with PEDOT:PSS) Immersed in NaCl and glycerol solution before measurement | 40 × 80 | 1.26 ± 0.18 KΩ | — | Tsukada et al., 2012 |

TABLE 3b

EC-12 test results for 3D printed electrodes

| Measurement Parameters | Internal Noise (μV) | Defibrillation discharge at 100 mV (5/15/25/35) (mV) | DC offset voltage after test (mV) | References |
|---|---|---|---|---|
| Standard ANSI/AAMI EC12-2000 | <150 | <100 | <100 | Tsukada et al., 2019 |
| PEDOT:PSS/DALC (20/80) | 52.0 ± 6.0 | 0.4 ± 0.2 | 0.1 | This work |
| PEDOT:PSS/DALC (40/60) | 38.0 ± 7.0 | 0.5 ± 0.4 | 0.2 ± 0.1 | This work |
| PEDOT:PSS/DALC (70/30) | 55.2 ± 10.0 | 0.6 ± 0.3 | 0.4 ± 0.3 | This work |
| Ag/AgCl with adhesive gel | — | — | — | Tsukada et al., 2012 |
| PEDOT:PSS silk glycerol thread | — | — | — | Tsukada et al., 2012 |
| Hitoe ® electrode (polyester nanofibre yarn with PEDOT:PSS) Immersed in NaCl and glycerol solution before measurement | 1-3 | — | 0.0028 ± 0.0020 | Tsukada et al., 2012 |

Tsukada et al., 2019 herein refers to Tsukada, Y. T. et al. Validation of wearable textile electrodes for ECG monitoring. Heart Vessels 34, 1203-1211 (2019).

Tsukada et al., 2012 herein refers to Tsukada, s., Nakashima, H. & Toimitus, K. Conductive Polymer Combined Silk Fiber Bundle for Bioeletrical Signal Recording. PLOS ONE 7, e33689 (2012).

Conclusion

The conducting polymer ink showed good electrochemical performance in energy storage as well as body potential monitoring devices. This work paves a way forward to fabricate greener bioelectronics by using bio-based, high performance conducting ink and enables a step in the direction of green devices. Hence, the reduced need for cellulose nanofibrils, a low weight fraction of conducting polymer in 3D ink along with good processability and excellent properties provides scalable and affordable fabrication of fiber-based wearable electronics.

Example 4. Printed Microelectrode-Array (MEA) Devices

The inks developed herein can be used to measure and monitor potentials from different types of cells such as cardiomyocytes or neural cells. They can be cheaper than gold-based MEAs commercially available and also do not require patterning techniques for cleanroom fabrication of such devices. Hence, saving the cost as well as time for fabrication process of MEAs.

It will be apparent to those skilled in the art that various modifications and variations can be made in the disclosed devices and systems without departing from the scope of the disclosure. Other aspects of the disclosure will be apparent to those skilled in the art from consideration of the specification and practice of the features disclosed herein. It is intended that the specification and examples be considered as exemplary only. Many additional variations and modifications are possible and are understood to fall within the framework of the disclosure.

The invention claimed is:

1. A wearable absorbent article comprising:
at least one material layer; and
a conductor arrangement that is at least partially deposited on, optionally printed onto, the material layer,
wherein the conductor arrangement is formed from a composition comprising a dialcohol cellulose and an electrically conductive material.

2. The wearable absorbent article of claim 1, further comprising a sensing device, the conductor arrangement comprises the sensing device or a part of the sensing device, or wherein the wearable absorbent articles comprises a sensing device or a part of a sensing device that is in electrical contact with the conductor arrangement.

3. The wearable absorbent article of claim 2, wherein the sensing device comprises two elements and is configured to measure the resistance between two elements, or the sensing device is an impedance-based sensor.

4. The wearable absorbent article of claim 1, comprising:
a fluid absorption region for absorbing a fluid; and
an electronic device or a mounting position for mounting an electronic device,
wherein the conductor arrangement electrically connects the electronic device or the mounting position for mounting an electronic device to at least one sensing location for detecting wetness of the fluid absorption region.

5. The wearable absorbent article according to claim 4, wherein the fluid absorption region comprises an absorbent core, and
at least a part of the conductor arrangement is arranged so as to be electrically insulated from the absorbent core.

6. The wearable absorbent article according to claim 4, wherein the electronic device comprises a wetness detection unit that is removably attached to the remainder of the wearable absorbent article or is embedded within the remainder of the wearable absorbent article.

7. The wearable absorbent article according to claim 1, wherein the wearable absorbent article is a diaper, a sanitary towel, an incontinence garment, or a medical dressing.

8. The wearable absorbent article according to claim 7, further comprising at least one of a wound contacting layer, an absorbent core, and a backing layer.

9. The wearable absorbent article according to claim 1, wherein the conductor arrangement comprises a ground electrode and a capacitor electrode, the ground electrode forming a closed loop around the capacitor electrode.

10. The wearable absorbent article of claim 1, wherein the material layer comprises at least one item selected from a group consisting of flexible materials.

11. The wearable absorbent article according to claim 10, wherein the group consisting of flexible materials includes non-wovens, films, tissue paper and fabrics.

12. The wearable absorbent article according to claim 1, wherein the conductor arrangement comprises between 5 wt % and 70 wt % of the electrically active material, between 30 wt % and 95 wt % of the dialcohol cellulose, and, optionally, between 10 wt % and 80 wt % of a plasticizer.

13. The wearable absorbent article according to claim 1, wherein the electrically conductive material comprises a conductive polymer, the conductive polymer optionally comprising poly-3,4-ethylenedioxythiophene and polystyrene sulfonate.

14. The wearable absorbent article according to claim 1, wherein the conductor arrangement has an electric conductivity of at least 0.05 S/cm.

15. The wearable absorbent article according to claim 14, wherein the electric conductivity of the conductor arrangement is at least 0.1 S/cm, at least 0.5 S/cm, or at least 1 S/cm.

16. The wearable absorbent article according to claim 1, wherein the dialcohol cellulose comprises fibers having a diameter of at least 1 μm.

17. The wearable absorbent article according to claim 16, wherein the dialcohol cellulose comprises fibers having a diameter of at least 5 μm, at least 8 μm, or at least 12 μm.

18. A method of manufacturing a wearable absorbent article, comprising the steps of:
providing an absorbent article comprising at least one material layer; and
depositing a composition, comprising a dialcohol cellulose and an electrically conductive material, on the at least one material layer, to form a conductor arrangement on the at least one material layer.

19. The method of manufacturing a wearable absorbent article according to claim 18, wherein the composition is deposited on the at least one material layer by any one or several of the following techniques: 3D-printing, 2D-printing, screen printing, stencil printing, blade-coating, melt-processing molding, slot die coating, inkjet printing, laser printing, solution processing, vacuum filtration, solvent casting and paper making techniques, and
wherein, optionally, the composition is at least partly dried and/or cured before, during and/or after applying the composition.

20. The method of manufacturing a wearable absorbent article according to claim 18, wherein the method further comprises (an) additional step(s) of adding a cross-linking agent before, during and/or after applying the composition.

21. The method of manufacturing a wearable absorbent article according to claim 18, wherein a cross-linking agent is added before, during and/or after applying the composition.

22. An absorbent article manufactured according to claim 18.

* * * * *